United States Patent
Schnorr et al.

(10) Patent No.: US 6,815,192 B2
(45) Date of Patent: Nov. 9, 2004

(54) FAMILY 44 XYLOGLUCANASES

(75) Inventors: Kirk Schnorr, Holte (DK); Per Lina Jørgensen, Copenhagen (DK); Martin Schulein, Copenhagen (DK)

(73) Assignee: Novozymes A/S, Bagsvaerd (DK)

(*) Notice: Subject to any disclaimer, the term of this patent is extended or adjusted under 35 U.S.C. 154(b) by 0 days.

(21) Appl. No.: 09/784,554

(22) Filed: Feb. 16, 2001

(65) Prior Publication Data

US 2003/0032162 A1 Feb. 13, 2003

Related U.S. Application Data

(60) Provisional application No. 60/185,317, filed on Feb. 28, 2000.

(30) Foreign Application Priority Data

Feb. 24, 2000 (DK) .................... 2000 00291

(51) Int. Cl.$^7$ ............. C12P 21/06; C12N 9/00; C12N 9/44; C12N 15/00; C07H 21/04
(52) U.S. Cl. ............... 435/210; 435/4; 435/6; 435/69.1; 435/183; 435/200; 435/252.3; 435/320.1; 536/23.2; 536/23.7; 530/350
(58) Field of Search ............... 435/4, 6, 69.1, 435/183, 200, 210, 252.3, 320.1, 209, 262, 263; 536/23.2–23.7; 530/350; 510/114

(56) References Cited

U.S. PATENT DOCUMENTS 6,268,197 B1 * 7/2001 Schulein et al. ............ 435/209

FOREIGN PATENT DOCUMENTS

| EP | 0 921 188 A2 | 6/1999 |
|---|---|---|
| WO | WO 91/10732 | 7/1991 |
| WO | WO 91/17244 | 11/1991 |
| WO | 94/14953 | 7/1994 |
| WO | 98/38288 | 9/1998 |
| WO | 99/02663 | 1/1999 |

OTHER PUBLICATIONS

Vincken et al, Carbohydrate Research 298 (1997) 299–310.
Hansen et al., Bacteriol vol. 174 No. 11 pp 3522–3531, (Jun. 1992).

* cited by examiner

Primary Examiner—Manjunath N. Rao
(74) Attorney, Agent, or Firm—Elias J. Lombivis

(57) ABSTRACT

The present invention relates to xyloglucanases belonging to family 44 of glycosyl hydrolases and having a relative xyloglucanase activity of at least 30% between pH 5 and pH 8 are derived from the genus *Paenibacillus*, especially from a strain of *Paenibacillus polymyxa* or *Paenibacillus* sp. The xyloglucanases exhibit high performance in conventional detergent compositions.

33 Claims, No Drawings

SEQUENCE LISTING

```
<160> NUMBER OF SEQ ID NOS: 16

<210> SEQ ID NO 1
<211> LENGTH: 4059
<212> TYPE: DNA
<213> ORGANISM: Paenibacillus polymyxa

<400> SEQUENCE: 1
atgagggcga aaaatagtag taatcttttg ttcaaacgtt ccaaatggct gcctgtcgtc      60
atggcctgca cgatgatagt aggggggggct ttacctgctc cagctgtggt tcacggtcaa     120
acggcaaaga ctattactat taaagtagat acattcaagg atcgtaagcc tattagccct     180
tatatatacg gtacaaatca ggatttggca ggcgatgaaa atatggctgc cagacgactt     240
ggtggcaacc gaatgaccgg atacaactgg gaaaacaata tgtccaatgc aggaagtgac     300
tggcagcaat ctagcgataa ctatttatgc agtaatggtg gcctgacaca agccgaatgt     360
gaaaagccag gagcggtgac gacttcgttt catgaccaat cgctgaagct tggcacttat     420
tctttagtta cgttgccgat ggccggttat gtggctaagg atggaaacgg aagtgtgcag     480
gaaagcgaaa aggccccttc cgctcgttgg aatcaggtcg taaacgccaa aaatgcaccg     540
```

-continued

```
ttccaactac agcctgatct gaatgacaat cgggtctatg tggatgagtt cgtccatttt      600
ttagtgaaca agtacggcac tgcttcaaca aaggcggggg tgaaaggata tgccctcgac      660
aatgaacccg ctctctggtc gcatacgcac ccacgcattc atggtgaaaa agtcggagcg      720
aaagagttgg tagaccggtc agtcagttta tccaaagctg tgaaagcgat tgacgcgggg      780
gcagaggttt ttggcccggt tctttacgga tttggcgcct ataaagatct tcaaactgca      840
cctgattggg actctgtaaa aggcaattat agctggttcg tagactatta cctggatcaa      900
atgcgcctta gctcgcaagt cgaaggcaag agattgctgg atgtattcga cgtacactgg      960
tatcccgaag cgatgggcgg aggcatacga attacgaatg aggtaggcaa tgacgaaacg     1020
aagaaagcca gaatgcaggc acctcgcacc ttgtgggacc cgacctataa ggaagatagt     1080
tggatcgctc aatggaacag cgagtttttg cccatactac ctcgattgaa gcagtcggtg     1140
gataaatatt atccgggaac caagctggca atgaccgagt atagctatgg cggcgaaaat     1200
gatatttccg gcgggattgc gatgaccgat gtgctgggta tcttgggcaa aaatgatgtt     1260
tatatggcaa actactggaa gctaaaggat ggtgtcaaca actacgttag tgccgcttac     1320
aagctttatc gcaattatga cggaaaaaac tctactttcg gtgataccag tgttagtgcg     1380
caaacatcgg atattgtcaa tagctcggtc catgcttctg taacgaatgc atccgacaaa     1440
gaactgcatc tcgttgtcat gaataaaagc atggacagcg cattcgacgc ccaatttgat     1500
ctttccggcg cgaagactta catttccggt aaagtatggg ggttcgataa aaacagctcg     1560
caaattaaag aagcagcgcc aatcacgcaa atttcaggca accgttttac ttataccgta     1620
ccgcctttga cggcatatca cattgtgctg actactggca atgacacgtc tccagtggaa     1680
ggtcctgaaa gctttaagct gaaagctgag gctggtgatg ggaaagtcca tttatcctgg     1740
gatgcttcca gcggagttgt aggatacagc gtacagcggg caacagatga aaacggccct     1800
ttcactgctg tagcatccaa cttgaccgaa acgtcttata cggatactaa cgtgacaaac     1860
ggtacttcat actattacaa agtaaccgcc aaaaccaata agggatcgag cgaatccaat     1920
attttgaaag cggttccgaa gatgcctgta acggtcccg ctcgctatga agccgaagaa     1980
ggcacgctga agggaaccat tgtggaatcc agcgggaccg gctactccgg tgctggttat     2040
gtaacgaatt ccacaatccc aggggattct ctgacgatga cgattcaggc tcccacggca     2100
ggcttgtaca atcttacaat cggctaccgt tctcctcatg atgacaaacg caccaatttc     2160
tcattaaacg gcaaagcgtt tggcgaactg ctgcttaaga aaacggctga ttttaaagaa     2220
acttccggag gcaaggtgct gttgaatgca ggcgcgaata cgatcagttt tgaaacaggc     2280
tggggctggt acgatatcga ctacgtcaga ctggagcctg ccgctgaccg cccacctcat     2340
gcggtaacca aaacgcttac caatccgaat gcgacggtag aagcaaaagc attgatgaac     2400
tatctggttg atcaatacgg gaagaatatg ctctctggtc aagaggaaat aaacgaaatt     2460
gattggcttc aagccaatgt aggtaaaaag ccggcgattg cagcgcttga cctgatcgac     2520
tattcgccaa gcagagcgga acacggtctt agttccacag aggcagaaaa ggcgattgca     2580
tgggataagc aagggggat cgttaccttt gcatggcact ggaacgcacc gaaaggtctg     2640
atcgatacgc agggaaaaga atggtggaga ggcttctatg ccgattcaac cacattcgat     2700
atagaatatg cgatgaatca tccagagtcc gaagattata aattacttat tcgcgacatc     2760
gatgtgattg cagggcaatt gaagaagttg caggatgcga aggttcctgt cctgttccgt     2820
cctttgcacg aagcggaagg aaaatggttc tggtggggcg ccaaaggtcc tgagcctgtt     2880
```

-continued

```
aaaaagctgt atattttaat gcacgaccgt ttgacgaatg tgcacaaatt gaacaatctg    2940
atttgggtat ggaattctgt tgctccggat tggtatccgg gagacgagta tgtggatatt    3000
ttgagctttg actcttatcc gcaagcaggt gattacagcc cgcaaatttc aaaatacgaa    3060
gaccttgttg cattgggcaa ggacaaaaag ctagttgcca tgagcgaaaa tggaccgatc    3120
ccggaccctg atttgatgaa ggcgtatcaa gctcattgga gctggttcgc tacatgggtat   3180
```

```
aaaaagctgt atattttaat gcacgaccgt ttgacgaatg tgcacaaatt gaacaatctg    2940
atttgggtat ggaattctgt tgctccggat tggtatccgg gagacgagta tgtggatatt    3000
ttgagctttg actcttatcc gcaagcaggt gattacagcc cgcaaatttc aaaatacgaa    3060
gaccttgttg cattgggcaa ggacaaaaag ctagttgcca tgagcgaaaa tggaccgatc    3120
ccggaccctg atttgatgaa ggcgtatcaa gctcattgga gctggttcgc tacatgggtat   3180
ggagattttg tgagagacgg caaacaaaac agccttgagc atctgaaaaa agtgtataat    3240
catccgaacg tcattacgct ggatgagctc ccaacgaact taaaaacgta tggcattact    3300
gagcagccgt ccgtaccggg cagcttcacg ctgaacgctg cgggtgaaac ggcgaaagta    3360
tcgctaagct ggacagcatc ggcgaatgcg aaaagctatg aagtgaagcg ttcgacgact    3420
gaaaacggcg cgttcgccac tgtagcgagt gatgtatatg gcagtagcta caccgacaca    3480
gctgtaacgg cagatacgac gtactactac caagtcgtag cgaagaacga tgcaggacag    3540
acgctgtcga acacggctag cgcaatgccg aaagcggata ctcagcagcc gacgacagga    3600
ctgctgctcc aatatcgcac agcagatact aaggtgaacg ataatcacct caatccgcaa    3660
ttccaaattg taaacaaagg cacaacctcc ataccgatca acgagttgaa aattcgctac    3720
tactacacaa tcgacggtga ccgtgagcag actttcaact gcgactatgc gacgctgagc    3780
tgctcaaagc tgaacggtaa actggttaaa atggagaagg ctgcaaccgg tgccgattat    3840
tatttggaag tcagtttcaa ttcggatgca ggcgtgttag cacctggagg aagcacgggc    3900
gatatccaaa cccgtattca taagacagac tggtcgaact ataacgaaag tgacgattat    3960
tcgtataaag gcacgcaaac ctcatttgcc gatcatccta aagttacctt gtatcataac    4020
ggcgtacttg tttggggaac cgagccgaca gctaattaa                            4059
```

<210> SEQ ID NO 2
<211> LENGTH: 1352
<212> TYPE: PRT
<213> ORGANISM: Paenibacillus polymyxa

<400> SEQUENCE: 2

```
Met Arg Ala Lys Asn Ser Ser Asn Leu Leu Phe Lys Arg Ser Lys Trp
1               5                   10                  15

Leu Pro Val Val Met Ala Cys Thr Met Ile Val Gly Gly Ala Leu Pro
            20                  25                  30

Ala Pro Ala Val Val His Gly Gln Thr Ala Lys Thr Ile Thr Ile Lys
        35                  40                  45

Val Asp Thr Phe Lys Asp Arg Lys Pro Ile Ser Pro Tyr Ile Tyr Gly
    50                  55                  60

Thr Asn Gln Asp Leu Ala Gly Asp Glu Asn Met Ala Ala Arg Arg Leu
65                  70                  75                  80

Gly Gly Asn Arg Met Thr Gly Tyr Asn Trp Glu Asn Asn Met Ser Asn
                85                  90                  95

Ala Gly Ser Asp Trp Gln Gln Ser Ser Asp Asn Tyr Leu Cys Ser Asn
            100                 105                 110

Gly Gly Leu Thr Gln Ala Glu Cys Glu Lys Pro Gly Ala Val Thr Thr
        115                 120                 125

Ser Phe His Asp Gln Ser Leu Lys Leu Gly Thr Tyr Ser Leu Val Thr
    130                 135                 140

Leu Pro Met Ala Gly Tyr Val Ala Lys Asp Gly Asn Gly Ser Val Gln
145                 150                 155                 160

Glu Ser Glu Lys Ala Pro Ser Ala Arg Trp Asn Gln Val Val Asn Ala
```

-continued

```
              165                 170                 175
Lys Asn Ala Pro Phe Gln Leu Gln Pro Asp Leu Asn Asp Asn Arg Val
            180                 185                 190
Tyr Val Asp Glu Phe Val His Phe Leu Val Asn Lys Tyr Gly Thr Ala
            195                 200                 205
Ser Thr Lys Ala Gly Val Lys Gly Tyr Ala Leu Asp Asn Glu Pro Ala
            210                 215                 220
Leu Trp Ser His Thr His Pro Arg Ile His Gly Glu Lys Val Gly Ala
225                 230                 235                 240
Lys Glu Leu Val Asp Arg Ser Val Ser Leu Ser Lys Ala Val Lys Ala
            245                 250                 255
Ile Asp Ala Gly Ala Glu Val Phe Gly Pro Val Leu Gly Phe Gly
            260                 265                 270
Ala Tyr Lys Asp Leu Gln Thr Ala Pro Asp Trp Asp Ser Val Lys Gly
            275                 280                 285
Asn Tyr Ser Trp Phe Val Asp Tyr Tyr Leu Asp Gln Met Arg Leu Ser
            290                 295                 300
Ser Gln Val Glu Gly Lys Arg Leu Leu Asp Val Phe Asp Val His Trp
305                 310                 315                 320
Tyr Pro Glu Ala Met Gly Gly Ile Arg Ile Thr Asn Glu Val Gly
            325                 330                 335
Asn Asp Glu Thr Lys Lys Ala Arg Met Gln Ala Pro Arg Thr Leu Trp
            340                 345                 350
Asp Pro Thr Tyr Lys Glu Asp Ser Trp Ile Ala Gln Trp Asn Ser Glu
            355                 360                 365
Phe Leu Pro Ile Leu Pro Arg Leu Lys Gln Ser Val Asp Lys Tyr Tyr
370                 375                 380
Pro Gly Thr Lys Leu Ala Met Thr Glu Tyr Ser Tyr Gly Gly Glu Asn
385                 390                 395                 400
Asp Ile Ser Gly Gly Ile Ala Met Thr Asp Val Leu Gly Ile Leu Gly
            405                 410                 415
Lys Asn Asp Val Tyr Met Ala Asn Tyr Trp Lys Leu Lys Asp Gly Val
            420                 425                 430
Asn Asn Tyr Val Ser Ala Ala Tyr Lys Leu Tyr Arg Asn Tyr Asp Gly
            435                 440                 445
Lys Asn Ser Thr Phe Gly Asp Thr Ser Val Ser Ala Gln Thr Ser Asp
            450                 455                 460
Ile Val Asn Ser Ser Val His Ala Ser Val Thr Asn Ala Ser Asp Lys
465                 470                 475                 480
Glu Leu His Leu Val Val Met Asn Lys Ser Met Asp Ser Ala Phe Asp
            485                 490                 495
Ala Gln Phe Asp Leu Ser Gly Ala Lys Thr Tyr Ile Ser Gly Lys Val
            500                 505                 510
Trp Gly Phe Asp Lys Asn Ser Ser Gln Ile Lys Glu Ala Ala Pro Ile
            515                 520                 525
Thr Gln Ile Ser Gly Asn Arg Phe Thr Tyr Thr Val Pro Pro Leu Thr
            530                 535                 540
Ala Tyr His Ile Val Leu Thr Thr Gly Asn Asp Thr Ser Pro Val Glu
545                 550                 555                 560
Gly Pro Glu Ser Phe Lys Leu Lys Ala Glu Ala Gly Asp Gly Lys Val
            565                 570                 575
His Leu Ser Trp Asp Ala Ser Ser Gly Val Val Gly Tyr Ser Val Gln
            580                 585                 590
```

```
Arg Ala Thr Asp Glu Asn Gly Pro Phe Thr Ala Val Ala Ser Asn Leu
        595                 600                 605

Thr Glu Thr Ser Tyr Thr Asp Thr Asn Val Thr Asn Gly Thr Ser Tyr
    610                 615                 620

Tyr Tyr Lys Val Thr Ala Lys Thr Asn Lys Gly Ser Ser Glu Ser Asn
625                 630                 635                 640

Ile Leu Lys Ala Val Pro Lys Met Pro Val Asn Gly Pro Ala Arg Tyr
                645                 650                 655

Glu Ala Glu Glu Gly Thr Leu Lys Gly Thr Ile Val Glu Ser Ser Gly
            660                 665                 670

Thr Gly Tyr Ser Gly Ala Gly Tyr Val Thr Asn Phe His Asn Pro Gly
        675                 680                 685

Asp Ser Leu Thr Met Thr Ile Gln Ala Pro Thr Ala Gly Leu Tyr Asn
    690                 695                 700

Leu Thr Ile Gly Tyr Arg Ser Pro His Asp Asp Lys Arg Thr Asn Phe
705                 710                 715                 720

Ser Leu Asn Gly Lys Ala Phe Gly Glu Leu Leu Lys Lys Thr Ala
                725                 730                 735

Asp Phe Lys Glu Thr Ser Gly Gly Lys Val Leu Leu Asn Ala Gly Ala
                740                 745                 750

Asn Thr Ile Ser Phe Glu Thr Gly Trp Gly Trp Tyr Asp Ile Asp Tyr
            755                 760                 765

Val Arg Leu Glu Pro Ala Ala Asp Arg Pro Pro His Ala Val Thr Lys
    770                 775                 780

Thr Leu Thr Asn Pro Asn Ala Thr Val Glu Ala Lys Ala Leu Met Asn
785                 790                 795                 800

Tyr Leu Val Asp Gln Tyr Gly Lys Asn Met Leu Ser Gly Gln Glu Glu
                805                 810                 815

Ile Asn Glu Ile Asp Trp Leu Gln Ala Asn Val Gly Lys Lys Pro Ala
            820                 825                 830

Ile Ala Ala Leu Asp Leu Ile Asp Tyr Ser Pro Ser Arg Ala Glu His
    835                 840                 845

Gly Leu Ser Ser Thr Glu Ala Glu Lys Ala Ile Ala Trp Asp Lys Gln
850                 855                 860

Gly Gly Ile Val Thr Phe Ala Trp His Trp Asn Ala Pro Lys Gly Leu
865                 870                 875                 880

Ile Asp Thr Gln Gly Lys Glu Trp Trp Arg Gly Phe Tyr Ala Asp Ser
                885                 890                 895

Thr Thr Phe Asp Ile Glu Tyr Ala Met Asn His Pro Glu Ser Glu Asp
            900                 905                 910

Tyr Lys Leu Leu Ile Arg Asp Ile Asp Val Ile Ala Gly Gln Leu Lys
        915                 920                 925

Lys Leu Gln Asp Ala Lys Val Pro Val Leu Phe Arg Pro Leu His Glu
    930                 935                 940

Ala Glu Gly Lys Trp Phe Trp Trp Gly Ala Lys Gly Pro Glu Pro Val
945                 950                 955                 960

Lys Lys Leu Tyr Ile Leu Met His Asp Arg Leu Thr Asn Val His Lys
                965                 970                 975

Leu Asn Asn Leu Ile Trp Val Trp Asn Ser Val Ala Pro Asp Trp Tyr
            980                 985                 990

Pro Gly Asp Glu Tyr Val Asp Ile  Leu Ser Phe Asp Ser  Tyr Pro Gln
        995                 1000                1005
```

Ala Gly Asp Tyr Ser Pro Gln Ile Ser Lys Tyr Glu Asp Leu Val
1010             1015             1020

Ala Leu Gly Lys Asp Lys Lys Leu Val Ala Met Ser Glu Asn Gly
1025             1030             1035

Pro Ile Pro Asp Pro Asp Leu Met Lys Ala Tyr Gln Ala His Trp
1040             1045             1050

Ser Trp Phe Ala Thr Trp Tyr Gly Asp Phe Val Arg Asp Gly Lys
1055             1060             1065

Gln Asn Ser Leu Glu His Leu Lys Lys Val Tyr Asn His Pro Asn
1070             1075             1080

Val Ile Thr Leu Asp Glu Leu Pro Thr Asn Leu Lys Thr Tyr Gly
1085             1090             1095

Ile Thr Glu Gln Pro Ser Val Pro Gly Ser Phe Thr Leu Asn Ala
1100             1105             1110

Ala Gly Glu Thr Ala Lys Val Ser Leu Ser Trp Thr Ala Ser Ala
1115             1120             1125

Asn Ala Lys Ser Tyr Glu Val Lys Arg Ser Thr Thr Glu Asn Gly
1130             1135             1140

Ala Phe Ala Thr Val Ala Ser Asp Val Tyr Gly Ser Ser Tyr Thr
1145             1150             1155

Asp Thr Ala Val Thr Ala Asp Thr Thr Tyr Tyr Tyr Gln Val Val
1160             1165             1170

Ala Lys Asn Asp Ala Gly Gln Thr Leu Ser Asn Thr Ala Ser Ala
1175             1180             1185

Met Pro Lys Ala Asp Thr Gln Gln Pro Thr Thr Gly Leu Leu Leu
1190             1195             1200

Gln Tyr Arg Thr Ala Asp Thr Lys Val Asn Asp Asn His Leu Asn
1205             1210             1215

Pro Gln Phe Gln Ile Val Asn Lys Gly Thr Thr Ser Ile Pro Ile
1220             1225             1230

Asn Glu Leu Lys Ile Arg Tyr Tyr Tyr Thr Ile Asp Gly Asp Arg
1235             1240             1245

Glu Gln Thr Phe Asn Cys Asp Tyr Ala Thr Leu Ser Cys Ser Lys
1250             1255             1260

Leu Asn Gly Lys Leu Val Lys Met Glu Lys Ala Ala Thr Gly Ala
1265             1270             1275

Asp Tyr Tyr Leu Glu Val Ser Phe Asn Ser Asp Ala Gly Val Leu
1280             1285             1290

Ala Pro Gly Gly Ser Thr Gly Asp Ile Gln Thr Arg Ile His Lys
1295             1300             1305

Thr Asp Trp Ser Asn Tyr Asn Glu Ser Asp Asp Tyr Ser Tyr Lys
1310             1315             1320

Gly Thr Gln Thr Ser Phe Ala Asp His Pro Lys Val Thr Leu Tyr
1325             1330             1335

His Asn Gly Val Leu Val Trp Gly Thr Glu Pro Thr Ala Asn
1340             1345             1350

<210> SEQ ID NO 3
<211> LENGTH: 4056
<212> TYPE: DNA
<213> ORGANISM: Paenibacillus polymyxa

<400> SEQUENCE: 3
atgaaggcga aaaatagtag tagtatttgg tccaaacgtt ccaaatggct gcctgtcgtc    60

-continued

```
atggcatgca cgattatagt aggggtgct ctaccgactc caactgtagt tcacggtcaa      120
acggcaaaga ctgttaccat taaagtcgat acatccaagg atcgtaagcc tattagccct    180
tatatttacg gtacgaatca ggagttggca ggcgatgaga atctgactgc cagacgactt    240
ggtggcaatc gaatgaccgg atataactgg gaaaacaata tgtccaatgc aggaagcgac    300
tggatgcagt ccagcgatag ctatttatgc gacaacgccg gattgacaaa agccgaatgt    360
gaaaagccag gtgcggtggc aacctcgttt cacgatcaat cgctgaagca gggcacatat    420
tctttagtca cactgccgat ggccggttat gtggccaagg atggaaacgg aagtgtgcag    480
gaaagcgaaa aggctccttc cgctcggtgg aatgaggtcg taaacgctaa aaatgcgccg    540
tttcaattgc agcctgatct gaaagacaat caggtttatg cggatgaatt cgtcaacttt    600
ttagtgaaaa agtacggcgt tgcttcaaca aaaacgggcg tgaaaggata ctcgctcgac    660
aatgaacccg ctctctggtc gcatacgcat ccgcgcattc atggtgaaaa ggtcggagcg    720
aaagagttgg tagaccggtc ggtaagttta tccaaagccg ctaaggcggt tgacgcgggt    780
gcggaaattt ttgggcccgt tctttacggt tttggcgcct ataaagatct tcaaactgca    840
cctgattgga actctgtaaa aggcaactac agctggttcg tggactatta cctcgatcaa    900
atgcgcctca gctcgcaagc cgaaggcaag agattgctgg atgtcttcga tgtacactgg    960
tatcctgaag cgatgggcgg aggcatacga attacaaatg aggtaggcaa cgacgaaacg   1020
aagaaagcca gaatgcaagc gcctcgtact tgtgggatc cgacctacaa ggaagatagc    1080
tggatcgctc aatggaacag tgaattcttg cctttactgc ctcgattaaa gcagtcggtg   1140
gataagtatt acccgggaac caagctggct ttgactgagt atagctatgg tggcgaaaat   1200
gatatttccg gcggtatcgc tatggccgat gtgctgggca tcttgggcaa aaacgacgtt   1260
tatatggcaa actactggaa gttaaaggat ggtgccaaca actacgttag tgccgcttac   1320
aagctttacc gcaattatga cggaaaaagc tctactttcg gtgatatcag cgttcatgcg   1380
caaacgtcgg atattgttaa tagctcggtg catgcttccg taacggatgc atcctacaaa   1440
gaactgcacc tcgttgtcat gaataaaagc atggacagtg cattcgacgc ccaatttgat   1500 cttttccggcg agacgactta cggttccggt aaagtatggg gtttcgacaa aaatagctcg   1560
caaattaagg aagcagcgcc aatcacscaa atttcaggca accgytttac ctatacagta   1620
ccgcctttga cggcttatca catcgtgttg actgccggca atgatacacc tgtagaaaat   1680
cctgaaagct ttgcgctgag ggctgaggct ggcgatggaa agtcgattta tctgacgct    1740 tccagcggag ttgtaggtta cagcgtacag cgggcaacgt atgaaaacgg tccttttgct   1800
gctgtagcat ccaacttggt cgaaacgtct tatacggata cgaacgtaac gaacggcact   1860
tcttattatt ataaaataac cgcaaaaaca aagacgggaa cgagcgcatc caatgtcttg   1920
aaagcggttc cgcgggcgcc tgtagacggt ccggatcgct atgaagcgga agatggcacg   1980
ctgaagggga ccgttgtgga atccagtggg accggcttct ccggtactgg ttatgtaact   2040
aatttccaca atgcagggga ttccctgacg atgacgatcc aggctcccac ggcaggcttg   2100
tacaatctta caatcggata ccgttctcct catgatgaca aacgcacgaa tttctcttta   2160
aatggcaaag cgtctggaga gctggtactt tggaaaacgg ctgattttaa agaaacgtcc   2220
ggtggtaagg ttctgttgaa tgcagggcg aatacgatcg gttttgaaac aggctggggc   2280
tggtatgata tcgactacgt caagctggag ccagctgctg accgtccacc gcatgcggta   2340
acgaaaacgc tcatcaatcc gaatgcgaca gtagaagcaa aagcattgat gaactacctg   2400
gttgatcaat acgggaagaa tatgcttttcc ggtcaagagg atatgcccga aattgattgg   2460
```

-continued

```
cttcaagcga atgtaggtaa aaagccggct attgcggcac ttgacctgat tgactattcc    2520
ccaagcagag cggaacacgg tcttagttcc acagagacgg aaaaggcgat tgaatgggat    2580
aagcaagggg gcattgttac ctttgcatgg cactggaacg cgccgaaagg tctgatcgat    2640
acgcagggaa aagaatggtg gagaggcttc tatgccgatt cgactacatt cgatatagaa    2700
tatgcgatga atcatccaga gtccgaagat tataaattgc ttattcgcga catcgatgtg    2760
attgcagggc aattgaagaa gttgcaggat gcgaaagttc ctgtcctgtt ccgtcctttg    2820
cacgaagcgg agggcaaatg gttctggtgg ggcgctaaag gtcctgagcc tgttaaaaaa    2880
ttgtatattt tgatgcacga tcgtttgact aatgtgcaca aattgaacaa tctgatctgg    2940
gtctggaact ctgttgctcc cgactggtat ccgggagatg agtatgtgga tattttgagc    3000 tcgactctt atccgcaagc aggcgactac agcccgcaaa ttgcaaaata tgaagacctt    3060
gttacattgg gcaaggacaa aaagctagtt tgccatgagc gaaaacggac ctatcccgga    3120
cccggatctg atgaaggcgt atcaagccca ttggagctgg ttcgctacat ggtatgggga    3180
tttcttgaga cggcaaaac aaaacagtcc ttggagcatt tgaaaaagt gtataatcat    3240 ccgaacgtca ttacgcttga aaagctcccg actaacttaa aaacgtatgg cattaccgag    3300
caaccgtcag taccgggcag cttcacgctg aacgcagcgg gcgaaacggc gaaagtaaag    3360
ctgagctgga cagcatcagc gaatgcagca agctatgaag tgaagcgttc gacggttgaa    3420
aacggcgcgt tcgccacagt agcgagcgat gtatacggaa gcagctacac cgacacagcc    3480
gtaacagcag acacgacgta ctattaccaa gtcgtagcga agaacgatgc aggtcaaacg    3540
gtttcgaaca cggctagcgc agcgccgaaa gcggatactc agcagccgac aacgggattg    3600
gtgctccagt atcgcacagc ggatacaaat gtgaacgaca tcacttgaa cccgcatttc    3660 caaattttaa ataaaggtac aatctccgta ccgatcaacg agttgaaaat tcgctactac    3720
tacacgatcg acggtgaccg tgagcagaca ttcaactgcg actatgcggt gctgagctgc    3780
tcgaagctga atggtaagct ggttaaaatg gataaagctg caaccggtgc tgattattat    3840
ttggaagtca gcttcaactc ggatgcaggc gtgttagcct ctggaggaag cacgggcgga    3900
attcaaactc gtattcataa agcagactgg tcgaactata cgaaagtga cgattactcg    3960 tataaaggta cgcagacttc attcgacgat catacgaaag ctacgttgta tcacaatggc    4020
gtacttgttt ggggaaccga accgacagct aattaa                              4056
```

<210> SEQ ID NO 4
<211> LENGTH: 1350
<212> TYPE: PRT
<213> ORGANISM: Paenibacillus polymyxa

<400> SEQUENCE: 4

```
Met Lys Ala Lys Asn Ser Ser Ile Trp Ser Lys Arg Ser Lys Trp
1               5                   10                  15

Leu Pro Val Val Met Ala Cys Thr Ile Ile Val Gly Gly Ala Leu Pro
                20                  25                  30

Thr Pro Thr Val Val His Gly Gln Thr Ala Lys Thr Val Thr Ile Lys
            35                  40                  45

Val Asp Thr Ser Lys Asp Arg Lys Pro Ile Ser Pro Tyr Ile Tyr Gly
        50                  55                  60

Thr Asn Gln Glu Leu Ala Gly Asp Glu Asn Leu Thr Ala Arg Arg Leu
65                  70                  75                  80

Gly Gly Asn Arg Met Thr Gly Tyr Asn Trp Glu Asn Asn Met Ser Asn
```

-continued

```
                 85                  90                  95
Ala Gly Ser Asp Trp Met Gln Ser Ser Asp Ser Tyr Leu Cys Asp Asn
            100                 105                 110
Ala Gly Leu Thr Lys Ala Glu Cys Glu Lys Pro Gly Ala Val Ala Thr
            115                 120                 125
Ser Phe His Asp Gln Ser Leu Lys Gln Gly Thr Tyr Ser Leu Val Thr
            130                 135                 140
Leu Pro Met Ala Gly Tyr Val Ala Lys Asp Gly Asn Gly Ser Val Gln
145                 150                 155                 160
Glu Ser Glu Lys Ala Pro Ser Ala Arg Trp Asn Glu Val Val Asn Ala
            165                 170                 175
Lys Asn Ala Pro Phe Gln Leu Gln Pro Asp Leu Lys Asp Asn Gln Val
            180                 185                 190
Tyr Ala Asp Glu Phe Val Asn Phe Leu Val Lys Lys Tyr Gly Val Ala
            195                 200                 205
Ser Thr Lys Thr Gly Val Lys Gly Tyr Ser Leu Asp Asn Glu Pro Ala
            210                 215                 220
Leu Trp Ser His Thr His Pro Arg Ile His Gly Glu Lys Val Gly Ala
225                 230                 235                 240
Lys Glu Leu Val Asp Arg Ser Val Ser Leu Ser Lys Ala Ala Lys Ala
            245                 250                 255
Val Asp Ala Gly Ala Glu Ile Phe Gly Pro Val Leu Tyr Gly Phe Gly
            260                 265                 270
Ala Tyr Lys Asp Leu Gln Thr Ala Pro Asp Trp Asn Ser Val Lys Gly
            275                 280                 285
Asn Tyr Ser Trp Phe Val Asp Tyr Tyr Leu Asp Gln Met Arg Leu Ser
            290                 295                 300
Ser Gln Ala Glu Gly Lys Arg Leu Leu Asp Val Phe Asp Val His Trp
305                 310                 315                 320
Tyr Pro Glu Ala Met Gly Gly Gly Ile Arg Ile Thr Asn Glu Val Gly
            325                 330                 335
Asn Asp Glu Thr Lys Lys Ala Arg Met Gln Ala Pro Arg Thr Leu Trp
            340                 345                 350
Asp Pro Thr Tyr Lys Glu Asp Ser Trp Ile Ala Gln Trp Asn Ser Glu
            355                 360                 365
Phe Leu Pro Leu Leu Pro Arg Leu Lys Gln Ser Val Asp Lys Tyr Tyr
            370                 375                 380
Pro Gly Thr Lys Leu Ala Leu Thr Glu Tyr Ser Tyr Gly Gly Glu Asn
385                 390                 395                 400
Asp Ile Ser Gly Gly Ile Ala Met Ala Asp Val Leu Gly Ile Leu Gly
            405                 410                 415
Lys Asn Asp Val Tyr Met Ala Asn Tyr Trp Lys Leu Lys Asp Gly Ala
            420                 425                 430
Asn Asn Tyr Val Ser Ala Ala Tyr Lys Leu Tyr Arg Asn Tyr Asp Gly
            435                 440                 445
Lys Ser Ser Thr Phe Gly Asp Ile Ser Val His Ala Gln Thr Ser Asp
            450                 455                 460
Ile Val Asn Ser Ser Val His Ala Ser Val Thr Asp Ala Ser Tyr Lys
465                 470                 475                 480
Glu Leu His Leu Val Val Met Asn Lys Ser Met Asp Ser Ala Phe Asp
            485                 490                 495
Ala Gln Phe Asp Leu Ser Gly Glu Thr Thr Tyr Gly Ser Gly Lys Val
            500                 505                 510
```

-continued

Trp Gly Phe Asp Lys Asn Ser Ser Gln Ile Lys Glu Ala Ala Pro Ile
        515                 520                 525

Thr Gln Ile Ser Gly Asn Arg Phe Thr Tyr Thr Val Pro Pro Leu Thr
        530                 535                 540

Ala Tyr His Ile Val Leu Thr Ala Gly Asn Asp Thr Pro Val Glu Asn
545                 550                 555                 560

Pro Glu Ser Phe Ala Leu Arg Ala Glu Ala Gly Asp Gly Lys Ser Ile
                565                 570                 575

Tyr Leu Asp Ala Ser Ser Gly Val Val Gly Tyr Ser Val Gln Arg Ala
            580                 585                 590

Thr Tyr Glu Asn Gly Pro Phe Ala Ala Val Ala Ser Asn Leu Val Glu
        595                 600                 605

Thr Ser Tyr Thr Asp Thr Asn Val Thr Asn Gly Thr Ser Tyr Tyr Tyr
            610                 615                 620

Lys Ile Thr Ala Lys Thr Lys Thr Gly Thr Ser Ala Ser Asn Val Leu
625                 630                 635                 640

Lys Ala Val Pro Arg Ala Pro Val Asp Gly Pro Asp Arg Tyr Glu Ala
                645                 650                 655

Glu Asp Gly Thr Leu Lys Gly Thr Val Val Glu Ser Ser Gly Thr Gly
            660                 665                 670

Phe Ser Gly Thr Gly Tyr Val Thr Asn Phe His Asn Ala Gly Asp Ser
        675                 680                 685

Leu Thr Met Thr Ile Gln Ala Pro Thr Ala Gly Leu Tyr Asn Leu Thr
            690                 695                 700

Ile Gly Tyr Arg Ser Pro His Asp Asp Lys Arg Thr Asn Phe Ser Leu
705                 710                 715                 720

Asn Gly Lys Ala Ser Gly Glu Leu Val Leu Trp Lys Thr Ala Asp Phe
                725                 730                 735

Lys Glu Thr Ser Gly Gly Lys Val Leu Leu Asn Ala Gly Ala Asn Thr
            740                 745                 750

Ile Gly Phe Glu Thr Gly Trp Gly Trp Tyr Asp Ile Asp Tyr Val Lys
        755                 760                 765

Leu Glu Pro Ala Ala Asp Arg Pro Pro His Ala Val Thr Lys Thr Leu
770                 775                 780

Ile Asn Pro Asn Ala Thr Val Glu Ala Lys Leu Met Asn Tyr Leu
785                 790                 795                 800

Val Asp Gln Tyr Gly Lys Asn Met Leu Ser Gly Gln Glu Asp Met Pro
                805                 810                 815

Glu Ile Asp Trp Leu Gln Ala Asn Val Gly Lys Lys Pro Ala Ile Ala
            820                 825                 830

Ala Leu Asp Leu Ile Asp Tyr Ser Pro Ser Arg Ala Glu His Gly Leu
        835                 840                 845

Ser Ser Thr Glu Thr Glu Lys Ala Ile Glu Trp Asp Lys Gln Gly Gly
        850                 855                 860

Ile Val Thr Phe Ala Trp His Trp Asn Ala Pro Lys Gly Leu Ile Asp
865                 870                 875                 880

Thr Gln Gly Lys Glu Trp Trp Arg Gly Phe Tyr Ala Asp Ser Thr Thr
                885                 890                 895

Phe Asp Ile Glu Tyr Ala Met Asn His Pro Glu Ser Glu Asp Tyr Lys
            900                 905                 910

Leu Leu Ile Arg Asp Ile Asp Val Ile Ala Gly Gln Leu Lys Lys Leu
        915                 920                 925

-continued

```
Gln Asp Ala Lys Val Pro Val Leu Phe Arg Pro Leu His Glu Ala Glu
        930                 935                 940
Gly Lys Trp Phe Trp Trp Gly Ala Lys Gly Pro Glu Pro Val Lys Lys
945                 950                 955                 960
Leu Tyr Ile Leu Met His Asp Arg Leu Thr Asn Val His Lys Leu Asn
            965                 970                 975
Asn Leu Ile Trp Val Trp Asn Ser Val Ala Pro Asp Trp Tyr Pro Gly
        980                 985                 990
Asp Glu Tyr Val Asp Ile Leu Ser  Phe Asp Ser Tyr Pro  Gln Ala Gly
        995                 1000                1005
Asp Tyr  Ser Pro Gln Ile Ala  Lys Tyr Glu Asp Leu  Val Thr Leu
    1010                1015                1020
Gly Lys  Asp Lys Lys Leu Val  Cys His Glu Arg Lys  Arg Thr Tyr
    1025                1030                1035
Pro Gly  Pro Gly Ser Asp Glu  Gly Val Ser Ser Pro  Leu Glu Leu
    1040                1045                1050
Val Arg  Tyr Met Val Trp Gly  Phe Leu Glu Arg Arg  Gln Thr Lys
    1055                1060                1065
Gln Ser  Leu Glu His Leu Lys  Lys Val Tyr Asn His  Pro Asn Val
    1070                1075                1080
Ile Thr  Leu Glu Lys Leu Pro  Thr Asn Leu Lys Thr  Tyr Gly Ile
    1085                1090                1095
Thr Glu  Gln Pro Ser Val Pro  Gly Ser Phe Thr Leu  Asn Ala Ala
    1100                1105                1110
Gly Glu  Thr Ala Lys Val Lys  Leu Ser Trp Thr Ala  Ser Ala Asn
    1115                1120                1125
Ala Ala  Ser Tyr Glu Val Lys  Arg Ser Thr Val Glu  Asn Gly Ala
    1130                1135                1140
Phe Ala  Thr Val Ala Ser Asp  Val Tyr Gly Ser Ser  Tyr Thr Asp
    1145                1150                1155
Thr Ala  Val Thr Ala Asp Thr  Thr Tyr Tyr Gln Val  Val Ala
    1160                1165                1170
Lys Asn  Asp Ala Gly Gln Thr  Val Ser Asn Thr Ala  Ser Ala Ala
    1175                1180                1185
Pro Lys  Ala Asp Thr Gln Gln  Pro Thr Thr Gly Leu  Val Leu Gln
    1190                1195                1200
Tyr Arg  Thr Ala Asp Thr Asn  Val Asn Asp Asn His  Leu Asn Pro
    1205                1210                1215
His Phe  Gln Ile Leu Asn Lys  Gly Thr Ile Ser Val  Pro Ile Asn
    1220                1225                1230
Glu Leu  Lys Ile Arg Tyr Tyr  Tyr Thr Ile Asp Gly  Asp Arg Glu
    1235                1240                1245
Gln Thr  Phe Asn Cys Asp Tyr  Ala Val Leu Ser Cys  Ser Lys Leu
    1250                1255                1260
Asn Gly  Lys Leu Val Lys Met  Asp Lys Ala Ala Thr  Gly Ala Asp
    1265                1270                1275
Tyr Tyr  Leu Glu Val Ser Phe  Asn Ser Asp Ala Gly  Val Leu Ala
    1280                1285                1290
Ser Gly  Gly Ser Thr Gly Gly  Ile Gln Thr Arg Ile  His Lys Ala
    1295                1300                1305
Asp Trp  Ser Asn Tyr Asn Glu  Ser Asp Asp Tyr Ser  Tyr Lys Gly
    1310                1315                1320
Thr Gln  Thr Ser Phe Asp Asp  His Thr Lys Ala Thr  Leu Tyr His
```

-continued

```
            1325                1330                1335
Asn Gly Val Leu Val Trp Gly Thr Glu Thr Ala Asn
       1340                1345                1350
```

<210> SEQ ID NO 5
<211> LENGTH: 2141
<212> TYPE: DNA
<213> ORGANISM: Paenibacillus pabuli
<220> FEATURE:
<221> NAME/KEY: misc_feature
<222> LOCATION: (1)..(2141)
<223> OTHER INFORMATION: n is unknown nucleotide

<400> SEQUENCE: 5

| | | | | | |
|---|---|---|---|---|---|
| atgaaggcga | aaaatagtag | taatattttg | tccaaacgtt | ccaaatggct | gcctgtcgtc | 60 |
| atggcatgca | cgattatagt | agggggggct | ctaccggctc | caactgtagt | tcacggtcaa | 120 |
| acggcaaaga | ccgttaccat | taaagtcgat | acatccaagg | atcgtaagcc | tattagtcct | 180 |
| tatatatacg | gtacgaatca | ggatttggca | ggcgatgaaa | atctggctgc | cagacgactt | 240 |
| ggtggcaatc | gaatgaccgg | atacaactgg | aaaataata | tgtccaatgc | gggaagcgat | 300 |
| tggcagcaat | ctagcgataa | cttttttatgc | aacaatggtg | gcctgacaaa | agccgaatgt | 360 |
| gaaaagccgg | gagcagtgac | gacttcgttt | catgatcaat | cgctgaagct | gggcgcttat | 420 |
| tctttagtca | cgctgccgat | ggccggttat | gtggccaagg | atggaaacgg | aagtgtgcag | 480 |
| gaaagcgaac | aggctccttc | cgctcgttgg | aatcaggtcg | taaatgccaa | aaatgcgccg | 540 |
| ttccaactac | agcctgatct | gaatgacaat | caggtatatg | cggatgaatt | cgtcaatttt | 600 |
| ttagtgaaaa | agtacggcgc | tgcttcaaca | aaggcgggtg | tgaaaggata | tgcgctcgac | 660 |
| aatgaacccg | ctctctggtc | gcatacgcat | ccgcgcattc | atggtgaaaa | agtcnnnnnn | 720 |
| nnnnnnnnnn | nnnnnnnnnn | nnnnnnnnnn | nnnnnnnnnn | nnnnnnnnnn | nnnnnnnnnn | 780 |
| nnnnnnnnnn | nnnnnnnnnn | nnnnnnnnnn | nnnnnnnnnn | nnttcaaact | gcacntgatt | 840 |
| ggaacttctg | taaaggcaa | ctatagctgg | ttcgtggact | attacctgga | tcaaatgcgc | 900 |
| ctcaactcgc | aagccgaagg | caagagattg | ctggatgtat | cgatgtgca | ctggtatccc | 960 |
| gaagcgatgg | gcggaggcat | acgaattaca | aatgaggtag | gcaatgacga | aacgaagaaa | 1020 |
| gccagaatgc | aggcgcctcg | tactttgtgg | gaccccgacct | acaaggaaga | tagctggatc | 1080 |
| gctcaatgga | acagcgcatt | cttgccttta | ctgcctcgat | tgaagcagtc | ggtggacaag | 1140 |
| tattacccgg | gaaccaagct | ggctttgacc | gagtatagct | acggcggcga | aaatgatatt | 1200 |
| tccggcggta | ttgctatgac | cgatgtgctg | gcatcttgg | gcaaaaacga | cgtttatatg | 1260 |
| gcgaactatt | ggaagttaaa | ggatggtgcc | aacaactacg | ttagcgccgc | ttacaagctt | 1320 |
| taccgcaatt | atgacggaaa | aaacgctact | ttcggcgata | tcagcgttaa | tgcgcaaacg | 1380 |
| tcggatattg | ttaatagctc | ggtgcatgct | tccgtaacgg | atgcatccta | caaagaactg | 1440 |
| cacctcattg | tcatgaataa | agcatggac | agcgcattcg | acgcccaatt | cgatctttcc | 1500 |
| ggcgagacga | cttacagttc | cggtaaaata | tggggcttcg | ataaaaatag | ctcgcaaatt | 1560 |
| aaggcagtag | cgccaatcac | gcaaatttca | ggcaaccgct | ttacctatac | agtaccacct | 1620 |
| ttgacggctt | atcacatcgt | gttgactgcc | gacaatgata | cacctgtgcc | acctgtggaa | 1680 |
| gatcctgaaa | gctttacgct | gagggctgag | gctggcgatg | ggaaagtcga | tttgtcctgg | 1740 |
| gacgcttcca | gcggagttgt | gggttacagt | gtacagcggg | caacgtatga | aaacggtcct | 1800 |
| tttgctgctg | tagcatccaa | cttggtcgaa | acgtcttata | cggatacgaa | cgtaacgaac | 1860 |

-continued

```
ggcacttctt actattataa aataaccgca aaaacaaagg cgggaacgag cgaatccaat     1920
gtcttgaaag cggttccgcg aacgcctgta gacggcccgg atcgctatga agccgaagat     1980
ggcacgctga agggaaccat tgtggaatcc agcgggaccg gcttctccgg tactggttat     2040
gtaactaatt tccacaatgc agggattccc ctgacgatga cgatccacta gtgtcgacct     2100
gcaggcgcgc gagctccagc ttttgttccc tttagtgagg g                         2141
```

<210> SEQ ID NO 6
<211> LENGTH: 695
<212> TYPE: PRT
<213> ORGANISM: Paenibacillus pabuli
<220> FEATURE:
<221> NAME/KEY: MISC_FEATURE
<222> LOCATION: (1)..(695)
<223> OTHER INFORMATION: Xaa is an uknown amino acid

<400> SEQUENCE: 6

```
Met Lys Ala Lys Asn Ser Ser Asn Ile Leu Ser Lys Arg Ser Lys Trp
1               5                   10                  15

Leu Pro Val Val Met Ala Cys Thr Ile Ile Val Gly Gly Ala Leu Pro
            20                  25                  30

Ala Pro Thr Val Val His Gly Gln Thr Ala Lys Thr Val Thr Ile Lys
        35                  40                  45

Val Asp Thr Ser Lys Asp Arg Lys Pro Ile Ser Pro Tyr Ile Tyr Gly
 50                  55                  60

Thr Asn Gln Asp Leu Ala Gly Asp Glu Asn Leu Ala Ala Arg Arg Leu
65                  70                  75                  80

Gly Gly Asn Arg Met Thr Gly Tyr Asn Trp Glu Asn Asn Met Ser Asn
                85                  90                  95

Ala Gly Ser Asp Trp Gln Gln Ser Ser Asp Asn Phe Leu Cys Asn Asn
            100                 105                 110

Gly Gly Leu Thr Lys Ala Glu Cys Glu Lys Pro Gly Ala Val Thr Thr
        115                 120                 125

Ser Phe His Asp Gln Ser Leu Lys Leu Gly Ala Tyr Ser Leu Val Thr
    130                 135                 140

Leu Pro Met Ala Gly Tyr Val Ala Lys Asp Gly Asn Gly Ser Val Gln
145                 150                 155                 160

Glu Ser Glu Gln Ala Pro Ser Ala Arg Trp Asn Gln Val Val Asn Ala
                165                 170                 175

Lys Asn Ala Pro Phe Gln Leu Gln Pro Asp Leu Asn Asp Asn Gln Val
            180                 185                 190

Tyr Ala Asp Glu Phe Val Asn Phe Leu Val Lys Lys Tyr Gly Ala Ala
        195                 200                 205

Ser Thr Lys Ala Gly Val Lys Gly Tyr Ala Leu Asp Asn Glu Pro Ala
    210                 215                 220

Leu Trp Ser His Thr His Pro Arg Ile His Gly Glu Lys Val Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Phe Lys Leu His Xaa Ile Gly Thr Ser Val Lys Gly Asn Tyr
        275                 280                 285

Ser Trp Phe Val Asp Tyr Tyr Leu Asp Gln Met Arg Leu Asn Ser Gln
    290                 295                 300
```

```
Ala Glu Gly Lys Arg Leu Leu Asp Val Phe Asp Val His Trp Tyr Pro
305                 310                 315                 320

Glu Ala Met Gly Gly Ile Arg Ile Thr Asn Glu Val Gly Asn Asp
            325                 330                 335

Glu Thr Lys Lys Ala Arg Met Gln Ala Pro Arg Thr Leu Trp Asp Pro
            340                 345                 350

Thr Tyr Lys Glu Asp Ser Trp Ile Ala Gln Trp Asn Ser Ala Phe Leu
        355                 360                 365

Pro Leu Leu Pro Arg Leu Lys Gln Ser Val Asp Lys Tyr Tyr Pro Gly
        370                 375                 380

Thr Lys Leu Ala Leu Thr Glu Tyr Ser Tyr Gly Glu Asn Asp Ile
385                 390                 395                 400

Ser Gly Gly Ile Ala Met Thr Asp Val Leu Gly Ile Leu Gly Lys Asn
                405                 410                 415

Asp Val Tyr Met Ala Asn Tyr Trp Lys Leu Lys Asp Gly Ala Asn Asn
                420                 425                 430

Tyr Val Ser Ala Ala Tyr Lys Leu Tyr Arg Asn Tyr Asp Gly Lys Asn
            435                 440                 445

Ala Thr Phe Gly Asp Ile Ser Val Asn Ala Gln Thr Ser Asp Ile Val
450                 455                 460

Asn Ser Ser Val His Ala Ser Val Thr Asp Ala Ser Tyr Lys Glu Leu
465                 470                 475                 480

His Leu Ile Val Met Asn Lys Ser Met Asp Ser Ala Phe Asp Ala Gln
                485                 490                 495

Phe Asp Leu Ser Gly Glu Thr Thr Tyr Ser Ser Gly Lys Ile Trp Gly
            500                 505                 510

Phe Asp Lys Asn Ser Ser Gln Ile Lys Ala Val Ala Pro Ile Thr Gln
            515                 520                 525

Ile Ser Gly Asn Arg Phe Thr Tyr Thr Val Pro Pro Leu Thr Ala Tyr
530                 535                 540

His Ile Val Leu Thr Ala Asp Asn Asp Thr Pro Val Pro Pro Val Glu
545                 550                 555                 560

Asp Pro Glu Ser Phe Thr Leu Arg Ala Glu Ala Gly Asp Gly Lys Val
                565                 570                 575

Asp Leu Ser Trp Asp Ala Ser Ser Gly Val Val Gly Tyr Ser Val Gln
            580                 585                 590

Arg Ala Thr Tyr Glu Asn Gly Pro Phe Ala Ala Val Ala Ser Asn Leu
        595                 600                 605

Val Glu Thr Ser Tyr Thr Asp Thr Asn Val Thr Asn Gly Thr Ser Tyr
610                 615                 620

Tyr Tyr Lys Ile Thr Ala Lys Thr Lys Ala Gly Thr Ser Glu Ser Asn
625                 630                 635                 640

Val Leu Lys Ala Val Pro Arg Thr Pro Val Asp Gly Pro Asp Arg Tyr
                645                 650                 655

Glu Ala Glu Asp Gly Thr Leu Lys Gly Thr Ile Val Glu Ser Ser Gly
            660                 665                 670

Thr Gly Phe Ser Gly Thr Gly Tyr Val Thr Asn Phe His Asn Ala Gly
            675                 680                 685

Asp Ser Leu Thr Met Thr Ile
690                 695

<210> SEQ ID NO 7
<211> LENGTH: 42
<212> TYPE: DNA
```

```
<213> ORGANISM: Artificial sequence
<220> FEATURE:
<223> OTHER INFORMATION: Primer

<400> SEQUENCE: 7
gtcgccgggg cggccgctat caattggtaa ctgtatctca gc        42

<210> SEQ ID NO 8
<211> LENGTH: 64
<212> TYPE: DNA
<213> ORGANISM: Artificial sequence
<220> FEATURE:
<223> OTHER INFORMATION: Primer

<400> SEQUENCE: 8
gtcgcccggg agctctgatc aggtaccaag cttgtcgacc tgcagaatga ggcagcaaga    60
agat                                                                 64

<210> SEQ ID NO 9
<211> LENGTH: 61
<212> TYPE: DNA
<213> ORGANISM: Artificial sequence
<220> FEATURE:
<223> OTHER INFORMATION: Primer

<400> SEQUENCE: 9
gtcggcggcc gctgatcacg taccaagctt gtcgacctgc agaatgaggc agcaagaa     60 t                                                                   61

<210> SEQ ID NO 10
<211> LENGTH: 35
<212> TYPE: DNA
<213> ORGANISM: Artificial sequence
<220> FEATURE:
<223> OTHER INFORMATION: Primer

<400> SEQUENCE: 10
gtcggagctc tatcaattgg taactgtatc tcagc             35

<210> SEQ ID NO 11
<211> LENGTH: 35
<212> TYPE: DNA
<213> ORGANISM: Artificial sequence
<220> FEATURE:
<223> OTHER INFORMATION: Primer

<400> SEQUENCE: 11
aacagctgat cacgactgat cttttagctt ggcac             35

<210> SEQ ID NO 12
<211> LENGTH: 37
<212> TYPE: DNA
<213> ORGANISM: Artificial sequence
<220> FEATURE:
<223> OTHER INFORMATION: Primer

<400> SEQUENCE: 12
aactgcagcc gcggcacatc ataatgggac aaatggg           37

<210> SEQ ID NO 13
<211> LENGTH: 83
<212> TYPE: DNA
<213> ORGANISM: Artificial sequence
<220> FEATURE:
<223> OTHER INFORMATION: Primer
```

```
<400> SEQUENCE: 13
cgatcggccg ataaaaaaac cgggcggaaa ccgcccgtca tctggcgcgc ctatataccg    60
cggctgcaga atgaggcagc aag                                           83

<210> SEQ ID NO 14
<211> LENGTH: 25
<212> TYPE: DNA
<213> ORGANISM: Artificial sequence
<220> FEATURE:
<223> OTHER INFORMATION: Primer

<400> SEQUENCE: 14
ggcgcattaa cggaataaag ggtgt                                         25

<210> SEQ ID NO 15
<211> LENGTH: 39
<212> TYPE: DNA
<213> ORGANISM: Artificial sequence
<220> FEATURE:
<223> OTHER INFORMATION: Primer

<400> SEQUENCE: 15
gcattctgca gcagcggctg tggttcacgg tcaaacggc                          39

<210> SEQ ID NO 16
<211> LENGTH: 40
<212> TYPE: DNA
<213> ORGANISM: Artificial sequence
<220> FEATURE:
<223> OTHER INFORMATION: Primer

<400> SEQUENCE: 16
gctaggcgcg cctacactgg agacgtgtca ttgccagtag                         40
```

US 6,815,192 B2

FAMILY 44 XYLOGLUCANASES

CROSS-REFERENCE TO RELATED APPLICATIONS

This application claims priority of Danish application no. PA 2000 00291 filed Feb. 24, 2000 and U.S. provisional application No. 60/185,317 filed Feb. 28, 2000, the contents of which are incorporated herein by reference.

BACKGROUND OF THE INVENTION

1. Field of the Invention

The present invention relates to xyloglucanases belonging to family 44 of glycosyl hydrolases, preferably to enzymes exhibiting xyloglucanase activity as their major enzymatic activity in the neutral and alkaline pH ranges; to a method of producing such enzymes; and to methods for using such enzymes in the textile, detergent and cellulose fiber processing industries.

2. Description of Related Art

Xyloglucan is a major structural polysaccharide in the primary (growing) cell wall of plants. Structurally, xyloglucans consists of a cellulose-like beta-1,4-linked glucose backbone which is frequently substituted with various side chains. The xyloglucans of most dicotyledonous plants, some monocotyledons and gymnosperms are highly branched polysaccharides in which approx. 75% of the glucose residues in the backbone bear a glycosyl side chain at O-6. The glycosyl residue that is directly attached to the branched glucose residue is invariably alfa-D-xylose. Up to 50% of the side chains in the xyloglucans contain more than one residue due to the presence of beta-D-galactose or alfa-L-fucose-(1-2)-beta-D-galactose moieties at O-2 of the xylose residues (C. Ohsumi and T. Hayashi (1994) Plant and Cell Physiology 35:963–967; G. J. McDougall and S. C. Fry (1994) Journal of Plant Physiology 143:591–595; J. L. Acebes et al. (1993) Phytochemistry 33:1343–1345). On acid hydrolysis, the xyloglucan extracted from cotton fibers yielded glucose, xylose, galactose and fucose in the ratio of 50:29:12:7 (Hayashi et al., 1988).

Xyloglucans produced by solanaceous plants are unusual in that typical only 40% of the beta-1,4-linked glucose residues bear a glycosyl side chain at O-6. Furthermore, up to 60% of the xylose residues are substituted at O-2 with alfa-L-arabinose residues and some solanaceous plants, such as potato, also have xyloglucans with beta-D-galactose substituents at O-2 of some of the xylose residues (York et al (1996)).

Xyloglucan is believed to function in the primary wall of plants by cross linking cellulose-micro fibrils, forming a cellulose-xyloglucan network. This network is considered necessary for the structural integrity of primary cell walls (Carpita et al., 1993). Another important function of xyloglucan is to act as a repository for xyloglucan subunit oligo saccharides that are physiologically active regulators of plant cell growth. Xyloglucan subunits may also modulate the action of a xyloglucan endotransglycosylase (XET), a cell wall associated enzyme that has been hypothesized to play a role in the elongation of plant cell walls. Therefore xyloglucan might play an important role in wall loosening and consequently cell expansion (Fry et al., 1992).

The seeds of many dicotyledonous species contain xyloglucan as the major polysaccharide storage reserve. This type of xyloglucan, which is localized in massive thickenings on the inside of the seed cotyledon cell wall, is composed mainly of glucose, xylose and galactose (Rose et al., 1996).

Seeds of the tamarind tree *Tamarindus indica* became a commercial source of gum in 1943 when the gum was found useful as a paper and textile size. Sizing of jute and cotton with tamarind xyloglucan has been extensively practiced in Asia owing to the low cost of the gum and to its excellent properties. Food applications of tamarind xyloglucan include use in confections, jams and jellies and as a stabilizer in ice cream and mayonnaise (Whistler et al., 1993).

Xyloglucanase activity is not included in the classification of enzymes provided by the Enzyme Nomenclature (1992). Hitherto, this enzymatic activity has simply been classified as glucanase activity and has often been believed to be identical to cellulolytic activity (EC 3.2.1.4), i.e. activity against β-1,4-glycosidic linkages in cellulose or cellulose derivative substrates, or at least to be a side activity in enzymes having cellulolytic activity. However, a true xyloglucanase is a true xyloglucan specific enzyme capable of catalyzing the solubilisation of xyloglucan to xyloglucan oligosaccharides but which does not exhibit substantial cellulolytic activity, e.g. activity against the conventionally used cellulose-like substrates CMC (carboxymethylcellulose), HE cellulose and Avicel (microcrystalline cellulose). A xyloglucanase cleaves the beta-1,4-glycosidic linkages in the backbone of xyloglucan.

Xyloglucanase activity is disclosed in Vincken et al. (1997) wherein three different endoglucanases EndoI, EndoV and EndoVI from *Trichoderma viride* (similar to *T. reesei*) are characterized. EndoI, EndoV and EndoVI belongs to family 5, 7 and 12 of glycosyl hydrolases, respectively, see Henrissat, B. et al. (1991, 1993).

International Patent Publication WO 94/14953 discloses a family 12 xyloglucanase (EG II) cloned from the fungus *Aspergillus aculeatus* and expressed in the fungus *Aspergillus oryzae*.

International Patent Publication WO 99/02663 discloses xyloglucanases cloned from *Bacillus licheniformis* (family 12) and *Bacillus agaradhaerens* (family 5) and expressed in *Bacillus subtilis*.

It is an object of the present invention to provide an enzyme with a high xyloglucanase activity at an alkaline pH which xyloglucanase exhibits excellent performance in conventional detergent compositions.

SUMMARY OF THE INVENTION

The inventors have now found enzymes having substantial xyloglucanase activity, which enzymes belong to family 44 of glycosyl hydrolases and perform excellent in conventional detergent compositions, especially in liquid detergent compositions.

Accordingly, the present invention relates to an enzyme preparation comprising a xyloglucanase belonging to family 44 of glycosyl hydrolases and exhibiting a relative activity of at least 30% between pH 5.0 and 8.0.

The inventors have also succeeded in cloning and expressing a family 44 xyloglucanase. Accordingly, in further aspects the invention relates to a family 44 xyloglucanase which is (a) a polypeptide encoded by the DNA sequence of positions 121–1677 of SEQ ID NO:1, (b) a polypeptide produced by culturing a cell comprising the sequence of SEQ ID NO:1 under conditions wherein the DNA sequence is expressed, (c) a xyloglucanase enzyme having a sequence of at least 60% identity to positions 40–559 of SEQ ID NO:2 when identity is determined by GAP provided in the GCG program package using a GAP creation penalty of 3.0 and GAP extension penalty of 0.1, or (d) a polypeptide encoded by a DNA sequence that hybridizes to the DNA sequence of SEQ ID NO: 1 under medium stringency conditions, wherein the medium stringency conditions comprise hybridization in 5×SSC at 45° C. and washing in 2×SSC at 60° C.; or (e) a polypeptide encoded by the xyloglucanase encoding part of the DNA sequence obtainable from the plasmid in *Escherichia coli* DSM 13321; and to a family 44 xyloglucanase which is (a) a polypeptide encoded by the DNA sequence of positions 121–1677 of SEQ ID NO:3, (b) a polypeptide produced by culturing a cell comprising the sequence of SEQ ID NO:3 under conditions wherein the DNA sequence is expressed, or (c) a polypeptide encoded by the xyloglucanase encoding part of the DNA sequence obtainable from the plasmid in *Escherichia coli* DSM 13322; and to a family 44 xyloglucanase which is (a) a polypeptide encoded by the DNA sequence of positions 121–1677 of SEQ ID NO:5, (b) a polypeptide produced by culturing a cell comprising the sequence of SEQ ID NO:5 under conditions wherein the DNA sequence is expressed, or (c) a polypeptide encoded by the xyloglucanase encoding part of the DNA sequence obtainable from the plasmid in *Escherichia coli* DSM 13323; and to an isolated polynucleotide molecule encoding a polypeptide having xyloglucanase activity which polynucleotide molecule hybridizes to a denatured double-stranded DNA probe under medium stringency conditions, wherein the probe is selected from the group consisting of DNA probes comprising the sequence shown in positions 121–1677 of SEQ ID NO:1, 3 or 5, and DNA probes comprising a subsequence of positions 121–1677 of SEQ ID NO:1, 3 or 5, the subsequence having a length of at least about 100 base pairs.

In further aspects, the invention provides an expression vector comprising a DNA segment which is e.g. a polynucleotide molecule of the invention; a cell comprising the DNA segment or the expression vector; and a method of producing a exhibiting xyloglucanase enzyme, which method comprises culturing the cell under conditions permitting the production of the enzyme, and recovering the enzyme from the culture.

In yet another aspect the invention provides an isolated xyloglucanase enzyme characterized in (i) being free from homologous impurities and (ii) being produced by the method described above.

The novel enzyme of the present invention is useful for the treatment of cellulosic material, especially cellulose-containing fiber, yarn, woven or non-woven fabric. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising a xyloglucanase enzyme having substantial xyloglucanase activity in the neutral or alkaline range; and to use of the enzyme of the invention for the treatment of cellulose-containing fibers, yarn, woven or non-woven fabric.

The present invention has now made it possible to use a xyloglucanase in detergent compositions for removing or bleaching certain soils or stains present on laundry, especially soils and spots resulting from xyloglucan-containing food, plants, and the like. Further, it is contemplated that treatment with detergent compositions comprising the novel enzyme can prevent binding of certain soils to the xyloglucan left on the cellulosic material.

DETAILED DESCRIPTION OF THE INVENTION

Microbial Sources

For the purpose of the present invention the term "obtained from" or "obtainable from" as used herein in connection with a specific source, means that the enzyme is produced or can be produced by the specific source, or by a cell in which a gene from the source have been inserted.

It is at present contemplated that the xyloglucanase of the invention may be obtained from a gram-positive bacterium belonging to a strain of the genus Bacillus, in particular a strain of *Paenibacillus*.

In a preferred embodiment, the xyloglucanase of the invention is obtained from the strain *Paenibacillus polymyxa*, ATCC 832, which is publicly available from American Type Culture Collection (ATCC). This is the type strain of *Paenibacillus polymyxa*. It is at present contemplated that a DNA sequence encoding an enzyme with an amino acid sequence identity of at least 60% to the enzyme of the invention may be obtained from other strains belonging to the genus *Paenibacillus*.

Further, the strain *Paenibacillus* sp. was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 18, 2000 under the deposition number DSM 13329. The deposit was made by Novo Nordisk A/S and was later assigned to Novozymes A/S.

A plasmid comprising a DNA sequence encoding a xyloglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 16, 2000 under the deposition number DSM 13321. The deposit was made by Novo Nordisk A/S and was later assigned to Novozymes A/S. It is contemplated that the DNA sequence of this plasmid comprises the DNA sequence of SEQ ID NO: 1.

A plasmid comprising a DNA sequence encoding a xyloglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 16, 2000 under the deposition number DSM 13322. The deposit was made by Novo Nordisk A/S and was later assigned to Novozymes A/S. It is contemplated that the DNA sequence of this plasmid comprises the DNA sequence of SEQ ID NO: 3.

A plasmid comprising a DNA sequence encoding a xyloglucanase of the invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Feb. 16, 2000 under the deposition number DSM 13323. The deposit was made by Novo Nordisk A/S and was later assigned to Novozymes A/S. It is contemplated that the DNA sequence of this plasmid comprises the DNA sequence of SEQ ID NO: 5.

Definitions

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant xyloglucanase, but which microorganism simultaneously produces other enzymes, e.g. xyloglucanases, proteases, or cellulases, being naturally occurring fermentation products of the microorganism, i.e. the enzyme complex conventionally produced by the corresponding naturally occurring microorganism.

In the present context the term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector is to be introduced. Thus, the vector may be an autonomously replicating vector, i.e. a vector that exists as an extra chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Using an expression vector as described immediately above generally performs recombinant expression of a protein.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention), which originate from the homologous cell where the polypeptide of the invention is originally obtained.

The term "obtained from" as used herein in connection with a specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

Polynucleotides

Within preferred embodiments of the invention an isolated polynucleotide of the invention will hybridize to similar sized regions of SEQ ID NO: 1, SEQ ID NO: 3 or SEQ ID NO: 5, or a sequence complementary thereto, under at least medium stringency conditions.

In particular polynucleotides of the invention will hybridize to a denatured double-stranded DNA probe comprising either the full sequence shown in SEQ ID NO: 1 or the sequence shown in positions 121–1677 of SEQ ID NO: 1 or the full sequence shown in SEQ ID NO: 3 or the sequence shown in positions 121–1677 of SEQ ID NO: 3 or the partial sequence shown in SEQ ID NO: 5 or the sequence shown in positions 121–1677 of SEQ ID NO: 5 or any probe comprising a subsequence of SEQ ID NO: 5 or SEQ ID NO: 3 or SEQ ID NO:1 having a length of at least about 100 base pairs under at least medium stringency conditions, but preferably at high stringency conditions as described in detail below. Suitable experimental conditions for determining hybridization at medium or high stringency between a nucleotide probe and a homologous DNA or RNA sequence involve pre-soaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×10$^9$ cpm/μg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using an x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having endoglucanase activity of the invention are then identified and isolated by, for example, hybridization or PCR.

The present invention further provides counterpart polypeptides and polynucleotides from different bacterial strains (orthologs or paralogs). Of particular interest are xyloglucanase polypeptides from gram-positive alkalophilic strains, including species of Bacillus. Of special interest are xyloglucanase peptides from strains which are very closely related to the strain *Paenibacillus polymyxa*, ATCC 832, which is the type strain of *Paenibacillus polymyxa*.

Species homologes of a polypeptide with xyloglucanase activity of the invention can be cloned using information and compositions provided by the present invention in combination with conventional cloning techniques. For example, a DNA sequence of the present invention can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA sequence of the invention encoding an polypeptide having xyloglucanase activity can then be isolated by a variety of methods, such as by probing with probes designed from the sequences disclosed in the present specification and claims or with one or more sets of degenerate probes based on the disclosed sequences. A DNA sequence of the invention can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the xyloglucanase cloned from *Paenibacillus polymyxa*, e.g. from the type strain deposited as ATCC 832, or from *Paenibacillus* sp., DSM 13329, expressed and purified as described in Materials and Methods and Examples 1, 2 and 3, or by an activity test relating to a polypeptide having xyloglucanase activity.

Polypeptides

The sequence of amino acids nos. 40–559 of SEQ ID NO: 2, 4 and 6, respectively, is a mature xyloglucanase sequence of the catalytic active domain. The mature xyloglucanase sequence may in theory start at position 35 or 36 but the enzyme as such has the amino acid sequence starting at position 40 due to proteolytic maturing. Further, it should be noted that the genes disclosed herein (SEQ ID NOS: 1, 3, 5) in toto encodes multidomain enzymes, i.e. encodes a xyloglucanase domain (catalytic active domain), a mannanase domain (catalytic active domain) and a binding domain. However, only the part of the genes encoding the xyloglucanase domain is relevant for the present invention.

The present invention also provides xyloglucanase polypeptides that are substantially homologous to the polypeptide of amino acids nos. 40–559 of SEQ ID NO: 2, SEQ ID NO: 4 or SEQ ID NO: 6 and species homologs (paralogs or orthologs) thereof. The term "substantially homologous" is used herein to denote polypeptides having 60%, preferably at least 70%, more preferably at least 75%, more preferably at least 80%, more preferably at least 85%, and even more preferably at least 90%, sequence identity to the sequence shown in amino acids nos. 40–559 of SEQ ID NO: 2, 4 or 6 or their orthologs or paralogs. Such polypeptides will more preferably be at least 95% identical, and most preferably 98% or more identical to the sequence shown in amino acids nos. 40–559 of SEQ ID NO: 2, 4 or 6 or its orthologs or paralogs. Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1. The following sequence identity was found for the appended SEQ ID NOS: 2, 4 and 6:

SEQ ID #2 SEQ ID #4 SEQ ID #6
SEQ ID #2 100% 92% 84%

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a polypeptide of the invention having xyloglucanase activity.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the xyloglucanase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e xyloglucanase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photo affinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides, which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223, 409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 40 to 559 of SEQ ID NO: 2, 4 or 6 and retain the xyloglucanase activity of the wild-type protein.

The xyloglucanase enzyme of the invention may, in addition to the enzyme core comprising the catalytically domain, also comprise a cellulose binding domain (CBD), the cellulose binding domain and enzyme core (the catalytically active domain) of the enzyme being operably linked. The cellulose-binding domain (CBD) may exist as an integral part the encoded enzyme, or a CBD from another origin may be introduced into the xyloglucanase thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., op.cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the xyloglucanase and growing the host cell to express the fused gene. Enzyme hybrids may be described by the following formula:

CBD—MR—X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide encoded by the polynucleotide molecule of the invention.

Immunological Cross-reactivity

Polyclonal antibodies, especially monospecific polyclonal antibodies, to be used in determining immunological cross-reactivity may be prepared by use of a purified xyloglucanolytic enzyme. More specifically, antiserum against the xyloglucanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation $((NH_4)_2SO_4)$, followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Recombinant Expression Vectors

A recombinant vector comprising a DNA construct encoding the enzyme of the invention may be any vector, which may conveniently be subjected to recombinant DNA procedures, and the choice of vector will often depend on the host cell into which it is to be introduced. Thus, the vector may be an autonomously replicating vector, i.e. a vector that exists as an extra chromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence, which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The cloned DNA molecule introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the cloned DNA molecule or the recombinant vector of the invention is introduced may be any cell, which is capable of producing the desired enzyme and includes bacteria, yeast, fungi and higher eukaryotic cells.

Examples of bacterial host cells which on cultivation are capable of producing the enzyme of the invention may be a gram-positive bacteria such as a strain of Bacillus, in particular *Bacillus alkalophilus, Bacillus amyloliquefaciens, Bacillus brevis, Bacillus lautus, Bacillus lentus, Bacillus licheniformis, Bacillus circulans, Bacillus coagulans, Bacillus megatherium, Bacillus stearothermophilus, Bacillus subtilis* and *Bacillus thuringiensis*, a strain of Lactobacillus, a strain of Streptococcus, a strain of Streptomyces, in particular *Streptomyces lividans* and *Streptomyces murinus*, or the host cell may be a gram-negative bacteria such as a strain of *Escherichia coli*.

The transformation of the bacteria may be effected by protoplast transformation, electroporation, conjugation, or by using competent cells in a manner known per se (cf. e.g. Sambrook et al., supra).

When expressing the enzyme in bacteria such as *Escherichia coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as a strain of Bacillus or a strain of Streptomyces, the enzyme may be retained in the cytoplasm, or may be directed to the extra cellular medium by a bacterial secretion sequence.

Examples of a fungal host cell which on cultivation are capable of producing the enzyme of the invention is e.g. a strain of Aspergillus or Fusarium, in particular *Aspergillus awamori, Aspergillus nidulans, Aspergillus niger, Aspergillus oryzae,* and *Fusarium oxysporum,* and a strain of Trichoderma, preferably *Trichoderma harzianum, Trichoderma reesei* and *Trichoderma viride.*

Fungal cells may be transformed by a process involving protoplast formation and transformation of the protoplasts followed by regeneration of the cell wall in a manner known per se. The use of a strain of Aspergillus as a host cell is described in EP 238 023 (Novo Nordisk A/S), the contents of which are hereby incorporated by reference.

Examples of a host cell of yeast origin which on cultivation are capable of producing the enzyme of the invention is e.g. a strain of Hansenula sp., a strain of Kluyveromyces sp., in articular *Kluyveromyces lactis* and *Kluyveromyces marcianus,* a strain of Pichia sp., a strain of Saccharomyces, in particular *Saccharomyces carlsbergensis, Saccharomyces cerevisae, Saccharomyces kluyveri* and *Saccharomyces uvarum,* a strain of Schizosaccharomyces sp., in particular *Schizosaccharomyces pombe,* and a strain of Yarrowia sp., in particular *Yarrowia lipolytica.*

Examples of a host cell of plant origin which on cultivation are capable of producing the enzyme of the invention is e.g. a plant cell of *Solanum tuberosum* or *Nicotiana tabacum.*

Method of Producing a Xyloglucanolytic Enzyme

In another aspect, the present invention also relates to a method of producing the enzyme preparation of the invention, the method comprising culturing a microorganism capable of producing the xyloglucanase under conditions permitting the production of the enzyme, and recovering the enzyme from the culture. Culturing may be carried out using conventional fermentation techniques, e.g. culturing in shake flasks or fermentors with agitation to ensure sufficient aeration on a growth medium inducing production of the xyloglucanase enzyme. The growth medium may contain a conventional N-source such as peptone, yeast extract or casamino acids, a reduced amount of a conventional C-source such as dextrose or sucrose, and an inducer such as xyloglucan or composite plant substrates such as cereal bran (e.g. wheat bran or rice husk). The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

Further, the present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

As defined herein, an isolated polypeptide (e.g. an enzyme) is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

When an expression vector comprising a DNA sequence encoding the enzyme is transformed into a heterologous host cell it is possible to enable heterologous recombinant production of the enzyme of the invention.

Thereby it is possible to make a highly purified or monocomponent xyloglucanolytic composition, characterized in being free from homologous impurities.

In this present context "homologous impurities" means any impurities (e.g. other polypeptides than the enzyme of the invention), which originate from the homologous cell where the enzyme of the invention is originally obtained.

In the present invention the homologous host cell may be a strain of *Paenibacillus* sp. or *Paenibacillus polymyxa.*

The medium used to culture the transformed host cells may be any conventional medium suitable for growing the host cells in question. The expressed xyloglucanolytic enzyme may conveniently be secreted into the culture medium and may be recovered there from by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The present invention also relates to a transgenic plant, plant part or plant cell which has been transformed with a DNA sequence encoding the xyloglucanase of the invention so as to express and produce this enzyme in recoverable quantities. The enzyme may be recovered from the plant or plant part.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana.*

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g. based on when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are e.g. described by Tague et al, Plant, Phys., 86, 506, 1988.

For constitutive expression the 35S-CaMV promoter may be used (Franck et al., 1980. Cell 21: 285–294). Organ-specific promoters may e.g. be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promoter from a seed oil body protein (Chen et al., Plant and cell physiology vol. 39, No. 9 pp. 935–941 (1998), the storage protein napA promoter from *Brassica napus*, or any other seed specific promoter known in the art, e.g. as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, DW, Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well known in the art.

The Enzyme

In a preferred embodiment of the present invention, the xyloglucanase has a relative activity at a temperature of 50° C., referably of at least 60%, preferably at least 70%, compared to the activity at the optimal temperature.

In yet another preferred embodiment, at a temperature of 60° C., the relative xyloglucanase activity is at least 40%, preferably at least 50%; at a temperature of 70° C., the relative xyloglucanase activity is at least 40%, preferably at least 45%, especially at least 50%.

Enzyme Compositions

In a still further aspect, the present invention relates to an enzyme composition comprising an enzyme exhibiting xyloglucanase activity as described above.

The enzyme composition of the invention may, in addition to the xyloglucanase of the invention, comprise one or more other enzyme types, for instance hemicellulase such as xylanase and mannanase, cellulase or endo-$\beta$-1,4-glucanase components, chitinase, lipase, esterase, pectinase, cutinase, phytase, oxidoreductase (peroxidase, haloperoxidase, oxidase, laccase), protease, amylase, reductase, phenoloxidase, ligninase, pullulanase, pectate lyase, pectin acetyl esterase, polygalacturonase, rhamnogalacturonase, pectin lyase, pectin methylesterase, cellobiohydrolase, transglutaminase; or mixtures thereof.

The enzyme composition may be prepared in accordance with methods known in the art and may be in the form of a liquid or a dry composition. For instance, the enzyme composition may be in the form of a granulate or a micro-granulate. The enzyme to be included in the composition may be stabilized in accordance with methods known in the art.

Xyloglucanases have potential uses in a lot of different industries and applications. Examples are given below of preferred uses of the enzyme composition of the invention. The dosage of the enzyme composition of the invention and other conditions under which the composition is used may be determined based on methods known in the art.

The xyloglucanase or xyloglucanase composition according to the invention may be useful for at least one of the following purposes.

Uses

Use in the Detergent Industry

During washing and wearing, dyestuff from dyed fabrics or garment will conventionally bleed from the fabric, which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsown fabrics, including knits, wovens, denims, yarns, and towelling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

DETERGENT DISCLOSURE AND EXAMPLES

Surfactant System

The detergent compositions according to the present invention comprise a surfactant system, wherein the surfactant can be selected from non-ionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the non-ionic and/or anionic surfactants described herein.

Polyethylene, polypropylene, and polybutylene oxide conden-sates of alkyl phenols are suitable for use as the non-ionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available non-ionic surfactants of this type include Igepal™ CO-630, marketed by the GAF Corporation; and Triton™ X-45, X-114, X-100 and X-102, all marketed by the Rohm & Haas Company. These surfactants are commonly referred to as alkyl phenol alkoxylates (e.g., alkyl phenol ethoxylates).

The condensation products of primary and secondary aliphatic alcohols with about 1 to about 25 moles of ethylene oxide are suitable for use as the non-ionic surfactant of the non-ionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available non-ionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the non-ionic surfactant of the surfactant systems of the present invention are alkyl polysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkyl polyglycosides have the formula

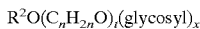

$R^2O(C_nH_{2n}O)_t(glycosyl)_x$ wherein $R^2$ is selected from the group consisting of alkyl, alkyl phenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional non-ionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the non-ionic surfactant of the non-ionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of non-ionic surfactant include certain of the commercially available Tetronic™ compounds, marketed by BASF.

Preferred for use as the non-ionic surfactant of the surfactant systems of the present invention are polyethylene oxide condensates of alkyl phenols, condensation products of primary and secondary aliphatic alcohols with from about 1 to about 25 moles of ethylene oxide, alkyl polysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred non-ionic surfactants are polyhydroxy fatty acid amide surfactants of the formula

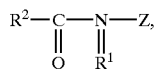

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxy hydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula RO(A)$_m$SO3M wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl, dimethyl, trimethyl-ammonium cations and quaternary ammonium cations such as tetramethyl-ammonium and dimethyl piperdinium cations and those derived from alkylamines such as ethylamine, diethyl amine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids), which are, sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

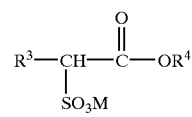

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation, which forms a water-soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula ROSO$_3$M wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono-, di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

[$R^2$ ($OR^3$)$_y$][$R^4$($OR^3$)$_y$]$_2R^5N+X$— wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$R_1R_2R_3R_4N^+X^-$ (i)

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

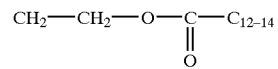

alkyl and $R_2R_3R_4$ are methyl).
di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

$$R^3(OR^4)_x N(R^5)_2$$
$$\overset{O}{\|}$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenleenschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadienide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000-5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include proteases, lipases, cutinases, amylases, cellulases, peroxidases, oxidases (e.g. laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename Opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a *Candida lipase*, such as a *C. antarctica* lipase, e.g., the *C. antarctica* lipase A or B described in EP 214 761, a *Pseudomonas lipase* such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus lipase*, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase (a and/or b) suitable for use in alkaline solutions can be used. Suitable amylases include those of bacterial or fungal origin. Chemically or genetically modified mutants are included. Amylases include, for example, a-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307 which discloses fungal cellulases produced from *Humicola insolens*, in WO 96/34108 and WO 96/34092 which disclose bacterial alkalophilic cellulases (BCE 103) from Bacillus, and in WO 94/21801, U.S. Pat. Nos. 5,475,101 and 5,419,778 which disclose EG III cellulases from Trichoderma. Especially suitable cellulases are the cellulases having colour care benefits. Examples of such cellulases are cellulases described in European patent application No. 0 495 257. Commercially available cellulases include Celluzyme™ and Carezyme™ produced by a strain of *Humicola insolens* (Novo Nordisk A/S), KAC-500 (B)™ (Kao Corporation), and Puradax™ (Genencor International).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases:Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching Agents

Additional optional detergent ingredients that can be included in the detergent compositions of the present invention include bleaching agents such as PB1, P4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. Nos. 4,483,781, 740,446, EP 0 133 354 and U.S. Pat. No. 4,412, 934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Pat. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", Nature 369, 1994, pp. 637–639.

Suds Suppressors

Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other Components

Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'disulphonate, disodium 4, -4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2,1,3-triazol-2-yl)-stilbene-2,2' disulphonate, di-so-dium 4,4'bis(2-anilino-4-(1-methyl-2-hydroxyethylamino)-s-triazin-6-ylami-no)stilene-2,2' disulphonate, sodium 2(stilbyl-4"-(naphtho-1', 2':4,5)-1,2,3,-triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

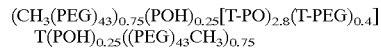

where PEG is —$(OC_2H_4)O$—, PO is $(OC_3H_6O)$ and T is $(pOOC_6H_4CO)$.

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric Dye-transfer Inhibiting Agents

The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinyl-pyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention. In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$–$C_{1Y}$ alkyl sulfate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1X}$–$C_{1Y}$ sodium alkyl sulfate condensed with an average of Z moles of ethylene oxide per mole |
| Nonionic: | $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula d-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF GmbH |
| Zeolite A: | Hydrated Sodium Aluminosilicate of formula $Na_{12}(AlO_2SiO_2)_{12}$. $27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2.H_2O_2$ |
| PB4: | Anhydrous sodium perborate tetrahydrate |
| Percarbonate: | Anhydrous sodium percarbonate bleach of empirical formula $2Na_2CO_3.3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N, N'-disuccinic acid, [S,S] isomer in the form of the sodium salt |
| Suds Suppressor: | 25% paraffin wax Mpt 50° C., 17% hydrophobic silica, 58% paraffin oil |
| Granular Suds suppressor: | 12% Silicone/silica, 18% stearyl alcohol, 70% starch in granular form |
| Sulphate: | Anhydrous sodium sulphate |
| HMWPEO: | High molecular weight polyethylene oxide |
| TAE 25: | Tallow alcohol ethoxylate (25) |

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |

-continued

| | |
|---|---|
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

The Xyloglucan Substrate

In addition to the aforesaid about xyloglucan it should be noted that xyloglucan from tamarind seeds supplied by Megazyme, Ireland has a complex branched structure with glucose, xylose, galactose and arabinose in the ratio of 45:36:16:3. Accordingly, it is strongly believed that an enzyme showing catalytic activity on this xyloglucan also has catalytic activity on other xyloglucan structures from different sources (angiosperms or gymnosperms).

Cotton suspension culture xyloglucan MW 100,000 kDa was obtained from Professor A. Mort of Oklahoma State University. 1H NMR (D2O, 80° C.) of xyloglucans was used to compare the monosaccharide composition of samples of different origin. The integrals of the anomeric signals from the commercial sample fully agree with the composition given by Megazyme. However, the cotton xyloglucan seems to have a different structure. There appears to be much less galactose and about half of galactose residues are fucosylated. Furthermore, the molar ratio between xylose and glucose is smaller (0.63 compared to 0.77 for the tamarind), which suggest a more open structure of cotton xyloglucan. These findings agree with results obtained with xyloglucan from cotton cells (Buchala et al, Acta Bot. Neerl. 42, 1993, 213–219).

| Xyloglucan | (Megazyme) | Cotton xyloglucan |
|---|---|---|
| Glucose | 45% | 52% |
| Xylose | 35% | 33% |
| Galactose | 16% | 10% |
| Fucose | — | 5% |
| Arabinose | <4% a | — | a Could not be detected in NMR

Materials and Methods

Strains Paenibacillus polymyxa, e.g. Paenibacillus polymyxa, ATCC 832, and Paenibacillus sp., DSM 13329, comprises a DNA sequence encoding a xyloglucanase of the invention.

Other Strains

E. coli hosts: XL1-Blue MRF⁻ and XLOLR E. coli strains were provided by Stratagene Inc. (USA) and used according to the manufacturer's instructions.

B. subtilis PL1885. (Diderichsen et al., (1990)).

B. subtilis PL1801. This strain is the B. subtilis DN1885 where the two major proteases have been inactivated (Diderichsen et al., (1990)).

Competent cells were prepared and transformed as described by Yasbin et al. (1975).

Plasmids pBK-CAMV: Stratagene inc. La Jolla Calif., USA.

Bacteriophage ZAP Express: Stratagene inc. La Jolla Calif., USA.

pMOL944. This plasmid is a pUB110 derivative essentially containing elements making the plasmid propagatable in Bacillus subtilis, kanamycin resistance gene and having a strong promoter and signal peptide cloned from the amyL gene of B. licheniformis ATCC 14580. The signal peptide contains a SacII site making it convenient to clone the DNA encoding the mature part of a protein in-fusion with the signal peptide. This results in the expression of a Pre-protein, which is directed towards the exterior of the cell.

The plasmid was constructed by means of ordinary genetic engineering and is briefly described in the following.

Construction of pMOL944

The pUB110 plasmid (McKenzie, T. et al., 1986,) was digested with the unique restriction enzyme NciI. A PCR fragment amplified from the amyL promoter encoded on the plasmid pDN1981 (Jørgensen et al., 1990) was digested with NciI and inserted in the NciI digested pUB110 to give the plasmid pSJ2624.

The two PCR primers used have the following sequences:

(SEQ ID NO:7)
LWN5494 5'-GTCGCCGGGGCGGCCGCTATCAATTGGTAACTGTATCT

CAGC-3'

(SEQ ID NO:8)
LWN5495 5'-GTCGCCCGGGAGCTCTGATCAGGTACCAAGCTTGTCGA
CCTGCAGAATGAGGCAGCAAGAAGAT-3'

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

(SEQ ID NO:9)
LWN5938 5'-GTCGGCGGCCGCTGATCACGTACCAAGCTTGTCGACCTG
CAGAATGAGGCAGCAAGAAGAT-3'

(SEQ ID NO:10)
LWN5939 5'-GTCGGAGCTCTATCAATTGGTAACTGTATCTCAGC-3'

The plasmid pSJ2670 was digested with the restriction enzymes PstI and BclI and a PCR fragment amplified from a cloned DNA sequence encoding the alkaline amylase SP722 (International Patent Application published as WO095/26397 which is hereby incorporated by reference) was digested with PstI and BclI and inserted to give the plasmid pMOL944. The two primers used for PCR amplification have the following sequence:

(SEQ ID NO:11)
LWN7864
5'-AACAGCTGATCACGACTGATCTTTTAGCTTGGCAC-3'

(SEQ ID NO:12)
LWN7901
5'-AACTGCAGCCGCGGCACATCATAATGGGACAAATGGG-3'

The primer #LWN7901 inserts a SacII site in the plasmid.

pPL3143 : This plasmid is a pMol944 derivative in which a terminator has been inserted between the SacII and the NotI site in pMOL944. At the same time a new restriction site for cloning AscI has been inserted.

The plasmid was constructed by means of ordinary genetic engineering and is briefly described in the following.

Construction of pPL3 143 : The plasmid pMOL944 was digested with SacII and NotI . A PCR fragment generating a terminator was made using the two primers listed below and plasmid pMOL944 as template. This fragment was digested with EagI and SacII and inserted between the SacII and the NotI site in PMOL944 to create the plasmid pPL3143.

(SEQ ID NO:13)
Primer 130721:
5'-CGATCGGCCGATAAAAAAACCGGGCGGAAACCGCCCGTCATCTGGCG

CGCCTATATACCGCGGCTGCAGAATGAGGCAGCAAG-3'

(SEQ ID NO:14)
Primer 130722:
5'-GGCGCATTAACGGAATAAAGGGTGT-3'

Media

TY (as described in Ausubel, F. M. et al. 1995).

LB agar (as described in Ausubel, F. M. et al, 1995).

LBPG is LB agar supplemented with 0.5% Glucose and 0.05 M potassium phosphate, pH 7.0

AZCL-xyloglucan is added to LBPG-agar to 0.5%. AZCL-xyloglucan is from Megazyme, Ireland.

BPX media is described in EP 0 506 780 (WO 91/09129).

NZY agar (per liter) 5 g of NaCl, 2 g of MgSO4, 5 g of yeast extract, 10 g of NZ amine (casein hydrolysate), 15 g of agar; add deionized water to 1 liter, adjust pH with NaOH to pH 7.5 and autoclave.

NZY broth (per liter) 5 g of NaCl, 2 g of MgSO4, 5 g of yeast extract, 10 g of NZ amine (casein hydrolysate); add deionized water to 1 liter, adjust pH with NaOH to pH 7.5 and autoclave NZY Top Agar (per liter) 5 g of NaCl, 2 g of MgSO4, 5 g of yeast extract, 10 g of NZ amine (casein hydrolysate), 0.7% (w/v) agarose; add deionized water to 1 liter, adjust pH with NaOH to pH 7.5 and autoclave.

Xyloglucanase Assay (XyloU)

The xyloglucanase activity is measured using AZCL-xyloglucan from Megazyme, Ireland, as substrate.

A solution of 0.2% of the blue substrate is suspended in a 0.1 M phosphate buffer pH 7.5 under stirring. The solution is distributed under stirring to 1.5 ml Eppendorf tubes (0.75 ml to each), 50 µl enzyme solution is added and they are incubated in an Eppendorp Thermomixer model 5436 for 20 minutes at 40° C. with a mixing of 1200 rpm. After incubation the colored solution is separated from the solid by 4 minutes centrifugation at 14,000 rpm and the absorbance of the supernatant is measured at 600 nm.

One XyloU unit is defined as the amount of enzyme resulting in an absorbance of 0.24 in a 1 cm cuvette at 600 nm.

General Molecular Biology Methods

DNA manipulations and transformations were performed using standard methods of molecular biology (Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

The following examples illustrate the invention.

Example 1

Cloning of Xyloglucanase Encoding Genes From *Paenibacillus* Species

Genomic DNA Preparation

Strains of *Paenibacillus polymyxa*, including *Paenibacillus polymyxa*, ATCC 842, and the strain *Paenibacillus* sp., DSM 13329, respectively, were propagated in liquid TY medium. After 16 hours incubation at 30° C. and 300 rpm, the cells were harvested, and genomic DNA isolated by the method described by Pitcher et al. (1989).

Genomic Library Construction

Lambda ZAP libraries were prepared from genomic DNA of the strains *Paenibacillus polymyxa, Paenibacillus polymyxa*, ATCC 842, *Paenibacillus* sp., DSM 13329. The ZAP Express cloning kit used was with BamHI digested and dephosphorylated arms from Stratagene. Isolated DNA was partially digested with Sau3A and size fractionated on a 1% agarose gel. DNA was excised from the agarose gel between 3 and 10 Kb and purified using Qiaspin DNA fragment purification procedure (Qiagen GmbH). 100 ng of purified, fractionated DNA was ligated with 1 µg of BamHI dephosphorylated ZAPexpress vector arms (4 degrees overnight). Ligation reaction was packaged directly with GigaPackIII Gold according to the manufacturers instructions (Stratagene). Phage libraries were titered with XL1blue mrf⁻ (Stratagene).

Screening for Xyloglucanase Clones by Functional Expression in lambdaZAPExpress

Approximately 10,000 plaque-forming units (pfu) from the genomic library were plated on NZY-agar plates containing 0.1% AZCL-xyloglucan (MegaZyme, Ireland), using *E. coli* XL1-Blue MRF' (Stratagene, USA) as a host, followed by incubation of the plates at 37° C. for 24 hours. Xyloglucanase-positive lambda clones were identified by the formation of blue hydrolysis halos around the positive phage clones. These were recovered from the screening plates by coring the TOP-agar slices containing the plaques of interest into 500 µl of SM buffer and 20 µl of chloroform. The xyloglucanase-positive lambdaZAPExpress clones were plaque-purified by plating an aliquot of the cored phage stock on NZY plates containing 0.1% AZCL-xyloglucan as above. Single xyloglucanase-positive lambda clones were cored into 500 µl of SM buffer and 20 µl of chloroform, and purified by one more plating round as described above.

Single-clone in vivo Excision of the Phagemids from the Xyloglucanase-positive lambdaZAPExpress Clones

*E. coli* XL1-Blue cells (Stratagene, La Jolla Calif.) were prepared and resuspended in 10 mM MgSO4 as recommended by Stratagene (La Jolla, USA). 250 µl aliquots of the pure phage stocks from the xyloglucanase-positive clones were combined in and >$10^6$ pfu/ml of the ExAssist M13 helper phage (Stratagene), and the mixtures were incubated at 37° C. for 15 minutes. 3 ml of NZY broth was added to each tube and the tubes were incubated at 37° C. for 2.5 hours. The tubes were heated at 65° C. for 20 minutes to kill the *E. coli* cells and bacteriophage lambda; the phagemids being resistant to heating. The tubes were spun at 3000 rpm for 15 minutes to remove cellular debris and the supernatants were decanted into clean Falcon 2059 tubes. Aliquots of the supernatants containing the excised single-stranded phagemids were used to infect 200 µl of *E. coli* XLOLR cells (Stratagene, OD600=1.0 in 10 mM MgSO4) by incubation at 37° C. for 15 minutes. 350 µl of NZY broth was added to the cells and the tubes were incubated for 45 min at 37° C. Aliquots of the cells were plated onto LB kanamycin agar plates and incubated for 24 hours at 37° C. Five excised single colonies were re-streaked onto LB kanamycin agar plates containing 0.1% AZCL-xyloglucan (Megazyme, Australia). The xyloglucanase-positive phagemid clones were characterized by the formation of blue hydrolysis halos around the positive colonies. These were further analysed by restriction enzyme digests of the isolated phagemid DNA (QiaSpin kit, Qiagen, USA) with EcoRI, PstI, EcoRI-PstI, and HindIII followed by agarose gel electrophoresis.

Nucleotide Sequence Analysis

The nucleotide sequence of the genomic xyloglucanase clones were determined from both strands by the dideoxy chain-termination method (Sanger et al. (1977)) using 500 ng of Qiaspin-purified template (Qiagen, USA), the Taq deoxy-terminal cycle sequencing kit (Perkin-Elmer, USA), fluorescent labelled terminators and 5 pmol of either pBK-CMV polylinker primers (Stratagene, USA) or custom synthetic oligonucleotide primers. DNA sequence assembly was performed with the DNA Star package (www.DNASTAR.com).

Example 2

Subcloning and Expression in *B. subtilis* of the Xyloglucanase Core Part of the XYG1006 Multidomain Gene (Hereafter Called XYG1006) from *Paenibacillus polymyxa* Encoding for the Enzyme of the Invention In order to express the xyloglucanase enzyme core part of the XYG1006 multidomain enzyme the following PCR cloning scheme was followed. This cloning makes a translational fusion between the Amylase signal peptide on pPL3143 and the mature part of the XYG1006 multidomain enzyme. At the same time it creates an artificial translational stop codon corresponding to the amino acid number 560 in the XYG1006 multidomain gene.

The XYGl1006 encoding DNA sequence was PCR amplified using the PCR primer set consisting of these two oligo nucleotides:

(SEQ ID NO:15)
XYG1006 .upper.PstI
5'-GCATT<u>CTGCAG</u>CAGCGGCTGTGGTTCACGGTCAAACGGC-3'

(SEQ ID NO:16)
XYG1006 .lower.AscI
5'-GCTA<u>GGCGCGCC</u>TACACTGGAGACGTGTCATTGCCAGTAG-3'

Restriction sites PstI and AscI are underlined.

pXYG1006 plasmid DNA from *E. coli*, DSM 13321, was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatine) containing 200 µM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 1,6 kb indicated proper amplification of the gene segment.

Subcloning of PCR Fragment

Forty-five µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pPL3143 and twenty-five-µl of the purified PCR fragment was digested with PstI and AscI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the PstI-AscI digested and purified pPL3143. The ligation was performed overnight at 16° C. using 0.5 µg of each DNA fragment, 1 U of T4 DNA ligase and T4 ligase buffer (Boehringer Mannheim, Germany).

The ligation mixture was used to transform competent *B. subtilis* PL1801 cells. The transformed cells were plated onto LBPG agar plates containing 10 µg/ml of Kanamycin and 0.2% AZCL-Xyloglucan(Megazyme). After 18 hours incubation at 37° C. colonies were seen on plates. Several clones showing a blue halo around the colony were analyzed by isolating plasmid DNA from overnight culture broth.

One such positive clone was re-streaked several times on agar plates as used above, this clone was called PL3344. The clone PL3344 was grown overnight in TY-10 µg/ml Kanamycin at 37° C. The following day, 1 ml of cells were used to isolate plasmid from the cells using the Qiaprep Spin Plasmid Miniprep Kit #27106 according to the manufacturers recommendations for *B. subtilis* plasmid preparations.

This DNA was DNA sequenced and revealed the DNA sequence corresponding to the mature part of the *Paenibacillus polymyxa* xyloglucanase encoding domain correctly inserted into the pPL3143 cloning vector (Domain 1-1680 of SEQ ID NO: 1. The *Bacillus subtilis* strain PL3344 is thus containing a plasmid enabling the expression of the xyloglucanase domain of the XYG1006 multi domain gene. The translation product is thus from amino acid number 1 to 559(SEQ ID no: 2) which after cleavage of the signal peptide is expected to be secreted from *B. subtilis* as a protein spanning from amino acid 36 to 559(SEQ ID no: 2).

PL3344 was grown in 25×200 ml BPX media with 10 µg/ml of Kanamycin in two 500 ml baffled shake flasks for 5 days at 37° C. at 300 rpm.

Example 3

Purification and Characterization of Xyloglucanase from *Paenibacillus polymyxa*

The clone XYG1006 obtained as described in example 2 (PL3344 expressed in *B. subtilis*) was incubated in 4500 ml of PS-1 containing mg/ml kanamycin from shake flasks with a final pH of 5.5.

The fermentation medium was flocculated using cationic flocculation agent C521 (10% solution) and 0.1% solution of anionic agent A130: To 4500 ml of broth, 200 ml of C521 was added (10%) simultaneously with 400 ml of A130 (0.1%) under constant stirring at room temperature. The flocculated material was separated by centrifugation using a Sorval RC 3B centrifuge at 4,500 rpm for 30 minutes. The supernatant was adjusted to pH 7.0 using sodium hydroxide and then batch treated with 300 g of HPQ Sepharose equilibrated with 50 mM tris pH 7.0, and the unbound material was filter sterilized through a 0.7 µm filter.

The liquid was concentrated into 550 ml using filtron ultrafiltration with a MW cut off of 10 kDa. The concentrate was then diluted to 900 ml and passed over a S-Sepharose column equilibrated with 25 mM sodium acetate pH 5.0, and the not bound material was concentrated to 390 ml.

For obtaining a pure enzyme 2 ml of this partial pure enzyme was applied to a size chromatography (Superdex 75) column equilibrated with 0.1 M Sodium acetate pH 6.0. The xyloglucanase eluted as a single peak with a MW of 58 kDa in SDS-PAGE and with a specific activity of 255 XyloU units per mg protein.

The cloned xyloglucanase of the invention was used for raising rabbit antiserum.

After electroblotting of this band the N-terminal was determined as:

TAKTITIKVDTFKDRK (Amino Acids 41–56 of SEQ ID NO.:2)

This is in agreement with the amino acid sequence shown in SEQ ID NO: 2 deduced from the DNA sequence shown in SEQ ID NO: 1 with a 40 amino acid pro sequence. The calculated MW from the deduced sequence was 58 kDa and the calculated pI was 5.7. The molar extinction coefficient at 280 nm was 105,640.

The enzyme melted in the DSC (Differential Scanning Calorimeter) at 61.8° C. at pH 6.0.

The xyloglucanase showed optimal activity at 50° C. at pH 7.5 using the xylounits (XyloU) assay at different temperatures.

The xyloglucanase was more than 30% active between pH 5.0 and 8.0.

Kinetic determinations were performed using soluble tamarind gum xyloglucan at pH 7.5 and at 40° C., 20 minutes incubation time and measurement of the formation of reducing ends. The kCat of 220 per sec was determined. The kM was 0.2 g/l. The Michaelis-Menten kinetic values could be determined.

Example 4

Stability and Activity of *Paenibacillus polymyxa* Xyloglucanase in Commercial Liquid Detergents The xyloglucanase characterized in Example 3 was fully stable between pH 5 and 10 at room temperature, and had a half life of more than 50 days when incubated in a full formulated US liquid detergent as US Tide at 30° C. The xyloglucanase was fully active in the commercial US liquid detergent branded liquid Tide and in the commercial European liquid detergent branded liquid Ariel, using 20 min. incubation at 40° C.

Literatue

Ausubel, F. M. et al. (Eds.) "Current protocols in Molecular Biology". John Wiley and Sons, 1995.

N. C. Carpita and D. M. Gibeaut (1993) The Plant Journal 3:1–30.

T. Christensen et al. Biotechnology vol 6 page 1419–1422, 1988.

Devereux et al. (1984) Nucleic Acids Res. 12, 387–395.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

Dretzen, G., Bellard, M., Sassone-Corsi, P., Chambon, P. (1981) A reliable method for the recovery of DNA fragments from agarose and acrylamide gels. Anal. Biochem., 112, 295–298.

Eriksson, O. E. & Hawksworth, D. L.: Systema Ascomycetum vol 12 (1993).

S. C. Fry et al (1992) Biochemical Journal 282:821–828

Hawksworth, D. L., Kirk, P. M., Sutton, B. C. and Pegler, D. N.: Dictionary of the fungi, International Mycological Institute, 616 pp (1995);

T. Hayashi and D. P. Delmer (1988) Carbohydrate Research 181:273–277.

Henrissat, B. 1991. A classification of glycosyl hydrolases based on amino acid sequence similaritites. Biochem. J., 280:309–316.

Henrissat, B., and A. Bairoch. 1993. New families in the classification of glycosyl hydrolases based on amino acid sequence similaritites. Biochem. J., 293:781–788.

Jülich, W.: Higher Taxa of Basidiomycetes, Bibliotheca Mycologia 85, 485 pp (1981).

Jørgensen, P. L. et al., 1990, Gene, 96, p. 37–41.

McKenzie, T. et al., 1986, Plasmid 15:93–103.

Leatherbarrow, R. J. (1992) Grafit version 3.0 Erithacus Software Ltd. Staines, U.K.

Lever, M. (1972) A new reaction for colormetric determination of carbohydrates. Anal. Biochem. 47, 273–279.

O'Donnell, K.:Zygomycetes in culture, University of Georgia, US, 257 pp (1979).

Pitcher, D. G., Saunders, N. A., Owen, R. J. (1989). Rapid extraction of bacterial genomic DNA with guanidium thiocyanate. Lett. Appl. Microbiol., 8, 151–156.

J. K. C. Rose et al (1996) Plant Physiology 110:493–499

Sanger, F., Nicklen, S., and Coulson, A. R. (1977) Proc. Natl. Acad. Sci. U. S. A. 74, 5463–5467

A. L. Sonenshein, J. A. Hoch and Richard Losick (Eds.) (1993) *Bacillus subtilis* and other Gram-Positive Bacteria, American Society for microbiology, p.618.

Vincken, J. P., Beldman, G., and Voragen, A. G. J. Substrate-specificity of endoglucanases—what determines xyloglucanase activity. Carbohydrate Research 298(4):299–310, 1997.

Von Arx, J. A.: The genera of fungi sporulating in culture, 424 pp (1981).

R. L. Whistler and J. N. BeMiller (1993) Industrial gums: Polysaccharides and their derivatives, Academic Press Inc.

Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

W. S. York et al (1996) Carbohydrate Research 285:99–128.

---

What is claimed is:

1. An isolated xyloglucanase, which is
   (a) a polypeptide having an amino acid sequence that is at least 95% identical with one or more of the sequences of amino acids 40–559 of SEQ ID NO: 2, 4 or 6; or
   (b) a polypeptide encoded by a DNA sequence that hybridizes to one or more of nucleotides 121–1677 of SEQ ID NO: 1, 3 or 5, under high stringency conditions, wherein the high stringency conditions are defined as hybridization in 5×SSC at 45° C. and washing in 2×SSC at 70° C.

2. The xyloglucanase of claim 1, which has an amino acid sequence that is at least 95% identical with amino adds 40–559 of SEQ ID NO: 2.

3. The xyloglucanase of claim 2, which has an amino acid sequence that is at least 98% identical with amino acids 40–559 of SEQ ID NO: 2.

4. The xyloglucanase of claim 1, which comprises a sequence of amino acids 36–559 of SEQ ID NO: 2.

5. The xyloglucanase of claim 1, which comprises a sequence of amino acids 40–559 of SEQ ID NO: 2.

6. The xyloglucanase of claim 5, which consists of a sequence of amino acids 40–559 of SEQ ID NO: 2.

7. The xyloglucanase of claim 1, which has an amino acid sequence that is at least 95% identical with amino acids 40–559 of SEQ ID NO: 4.

8. The xyloglucanase of claim 7, which has an amino acid sequence that is at least 98% identical with amino acids 40–559 of SEQ ID NO: 4.

9. The xyloglucanase of claim 1, which comprises a sequence of amino acids 36–559 of SEQ ID NO: 4.

10. The xyloglucanase of claim 1, which comprises a sequence of amino acids 40–559 of SEQ ID NO: 4.

11. The xyloglucanase of claim 10, which consists of a sequence of amino acids 40–559 of SEQ ID NO: 4.

12. The xyloglucanase of claim 1, which has an amino acid sequence that is at least 95% identical with amino acids 40–559 of SEQ ID NO: 6.

13. The xyloglucanase of claim 12, which has an amino acid sequence that is at least 98% identical with amino acids 40–559 of SEQ ID NO: 6.

14. The xyloglucanase of claim 1, which comprises a sequence of amino acids 36–559 of SEQ ID NO: 6.

15. The xyloglucanase of claim 1, which comprises a sequence of amino acids 40–559 of SEQ ID NO: 6.

16. The xyloglucanase of claim 15, which consists of a sequence of amino acids 40–559 of SEQ ID NO: 6.

17. The xyloglucanase of claim 1, which is encoded by a DNA sequence that hybridizes to nucleotides 121–1677 of SEQ ID NO: 1 under high stringency conditions.

18. The xyloglucanase of claim 17, which is encoded by a DNA sequence that hybridizes to nucleotides 121–1677 of SEQ ID NO: 1 under high stringency conditions, wherein the high stringency conditions are defined as hybridization in 5×SSC at 45° C. and washing in 2×SSC at 75° C.

19. The xyloglucanase of claim 1, which is encoded by a DNA sequence that hybridizes to nucleotides 121–1677 of SEQ ID NO: 3 under high stringency conditions.

20. The xyloglucanase of claim 19, which is encoded by a DNA sequence that hybridizes to nucleotides 121–1677 of SEQ ID NO: 3 under high stringency conditions, wherein the high stringency conditions are defined as hybridization in 5×SSC at 45° C. and washing in 2×SSC at 75° C.

21. The xyloglucanase of claim 1, which is encoded by a DNA sequence that hybridizes to nucleotldes 121–1677 of SEQ ID NO: 5 under high stringency conditions.

22. The xyloglucanase of claim 21, which is encoded by a DNA sequence that hybridizes to nucleotides 121–1677 of SEQ ID NO: 5, under high stringency conditions, wherein the high stringency conditions are defined as hybridization in 5×SSC at 45° C. and washing in 2×SSC at 75° C.

23. The xyloglucanase of claim 17, which is obtained from the Bacillus/Lactobacillus subdivision.

24. The xyloglucanase of claim 23, which is obtained from a species of *Paenibacillus*.

25. The xyloglucanase of claim 24, which is obtained from *Paenibacillus polymyxa*.

26. The xyloglucenase of claim 19, which is obtained from the Bacillus/Lactobacillus subdivsion.

27. The xyloglucanase of claim 26, which is obtained from a species of *Paenibacillus*.

28. The xyloglucanase of claim 27, which is obtained from *Paenibacillus polymyxa*.

29. The xyloglucanase of claim 21, which is obtained from the Bacillus/Lactobacillus subdivision.

30. The xyloglucanase of claim 29, which is obtained from a species of *Paenibacillus*.

31. The xyloglucanase of claim 30, which is obtained from *Paenibacillus polymyxa*.

32. A detergent composition comprising a xyloglucanase of claim 1 and a surfactant.

33. A process for washing a fabric, comprising treating the fabric during a washing cycle of a machine washing process with a washing solution which comprises a xyloglucanase of claim 1.

* * * * *